(12) United States Patent
Lambert et al.

(10) Patent No.: US 8,609,100 B2
(45) Date of Patent: Dec. 17, 2013

(54) METHOD FOR INHIBITING DENDRITIC CELL IMMUNORECEPTOR (DCIR)-MEDIATED HUMAN IMMUNODEFICIENCY VIRUS INFECTION COMPRISING ADMINISTERING ANTI-DCIR ANTIBODIES

(75) Inventors: Alexandra Lambert, Québec (CA); Caroline Gilbert, St-Augustin de Desmeures (CA); Michel J. Tremblay, Québec (CA)

(73) Assignee: Universite Laval, Quebec, Quebec (CA)

( * ) Notice: Subject to any disclaimer, the term of this patent is extended or adjusted under 35 U.S.C. 154(b) by 0 days.

(21) Appl. No.: 13/280,070

(22) Filed: Oct. 24, 2011

(65) Prior Publication Data

US 2012/0039894 A1 Feb. 16, 2012

Related U.S. Application Data

(63) Continuation of application No. 12/457,673, filed on Jun. 18, 2009, now abandoned.

(60) Provisional application No. 61/129,343, filed on Jun. 19, 2008.

(51) Int. Cl.
*A61K 39/395* (2006.01)
*C07K 16/00* (2006.01)

(52) U.S. Cl.
USPC ............... 424/144.1; 530/387.9; 530/388.73

(58) Field of Classification Search
None
See application file for complete search history.

(56) References Cited

U.S. PATENT DOCUMENTS 8,057,798 B2  11/2011  Zurawski et al.

OTHER PUBLICATIONS

Aarons, E. J., et al., 2001, Adaptation to blockade of human immunodeficiency virus type 1 entry imposed by the anti-CCR5 monoclonal antibody 2D7, Virol. 287:382-390.*
Bansal, G. P., 2007, A summary of the workshop on passive immunization using monoclonal antibodies for HIV/AIDS, held at the National Institute of Allergy and Infectious Diseases, Bethesda, Mar. 10, 2006, Biol. 35:367-371.*
Biswas, P., et al., 2007, Access denied? The status of co-receptor inhibition to counter HIV entry, Expert Opin. Pharmacother. 8(7):923-933.*
Cadogan, M., and A. G. Dalgleish, 2008, HIV immunopathogenesis and strategies for intervention, Lancet Infect. Dis. 8:675-684.*
Choudrhry, V., et al., 2006, Antibody-based inhibitors of HIV infection, Expert Opin. Biol. Ther. 6(5):523-531.*
Jekle, A., et al., 2010, Epitope switching as a novel escape mechanism of HIV to CCR5 monoclonal antibodies, Antimicrob. Agents Chemother. 54(2):734-741.*
Richard M, Thibault N, Veilleux P, Breton R, Beaulieu AD. The ITIM-bearing CLECSF6 (DCIR) is down-modulated in neutrophils by neutrophil activating agents. Biochem Biophys Res Commun. 2003;310:767-773.
Gilbert C, Barat C, Cantin R, Tremblay MJ. Involvement of Src and Syk tyrosine kinases in HIV-1 transfer from dendritic cells to CD4+ T lymphocytes. J Immunol. 2007;178:2862-2871.
Cantin R, Fortin JF, Lamontagne G, Tremblay M. The presence of host-derived HLA-DR1 on human immunodeficiency virus type 1 increases viral infectivity. J Virol. 1997;71:1922-1930.
Dornadula G, Zhang H, Shetty S, Pomerantz RJ. HIV-1 virions produced from replicating peripheral blood lymphocytes are more infectious than those from nonproliferating macrophages due to higher levels of intravirion reverse transcripts: implications for pathogenesis and transmission. Virology. 1999;253:10-16.
Bounou S, Dumais N, Tremblay MJ. Attachment of human immunodeficiency virus-1 (HIV-1) particles bearing host-encoded B7-2 proteins leads to nuclear factor-kappa B- and nuclear factor of activated T cells-dependent activation of HIV-1 long terminal repeat transcription. J Biol Chem. 2001;276:6359-6369.
Bates EE, Fournier N, Garcia E, et al. APCs express DCIR, a novel C-type lectin surface receptor containing an immunoreceptor tyrosine-based inhibitory motif. J Immunol. 1999;163:1973-1983.
Turville SG, Cameron PU, Handley A, et al. Diversity of receptors binding HIV on dendritic cell subsets. Nat Immunol. 2002;3:975-983.
Turville SG, Santos JJ, Frank I, et al. Immunodeficiency virus uptake, turnover, and 2-phase transfer in human dendritic cells. Blood. 2004;103:2170-2179.
Moris A, PajotA, Blanchet F, Guivel-Benhassine F, Salcedo M, Schwartz O. Dendritic cells and HIV-specific CD4+ T cells: HIV antigen presentation, T-cell activation, and viral transfer. Blood. 2006;108:1643-1651.
Wu L, Martin TD, Carrington M, KewalRamani VN. Raji B cells, misidentified as THP-1 cells, stimulate DC-SIGN-mediated HIV transmission. Virology. 2004;318:17-23.
Feinberg H, Guo Y, Mitchell DA, Drickamer K, Weis WI. Extended neck regions stabilize tetramers of the receptors DC-SIGN and DC-SIGNR. J Biol Chem. 2005;280:1327-1335.
Mitchell DA, Fadden AJ, Drickamer K. A Novel Mechanism of Carbohydrate Recognition by the C-type Lectins DC-SIGN and DC-SIGNR. Subunit Organization and Binding to Multivalent Ligands. J Biol Chem. 2001;276:28939-28945.

* cited by examiner

*Primary Examiner* — Jeffrey S. Parkin
(74) *Attorney, Agent, or Firm* — Fasken Martineau DuMoulin, LLP

(57) ABSTRACT

A cell surface molecule designated DCIR (for dendritic cells ImmunoReceptor), a member of a recently described family of DC-expressing C-type lectin receptors, has been shown to participate to the capture of human immunodeficiency virus (HIV) and promote infection in trans and in cis of autologous CD4(+) T cells from human immature monocyte-derived DC. The contribution of DCIR to these processes was revealed using DCIR-specific siRNAs and a polyclonal antibody specific for the carbohydrate recognition domain of DCIR. Therapeutic agents for HIV infection are therefore provided herein. These therapeutic agents are useful for impairing the interaction between DCIR and HIV and as such may be useful for treatment or prevention of HIV infection. Also provided are assays for identifying additional therapeutics agents for treatment or prevention HIV infection.

21 Claims, 8 Drawing Sheets

Figure 5
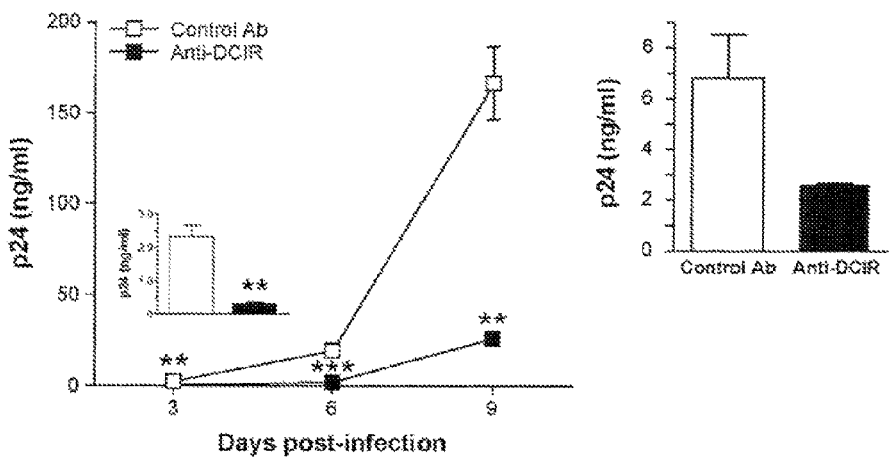
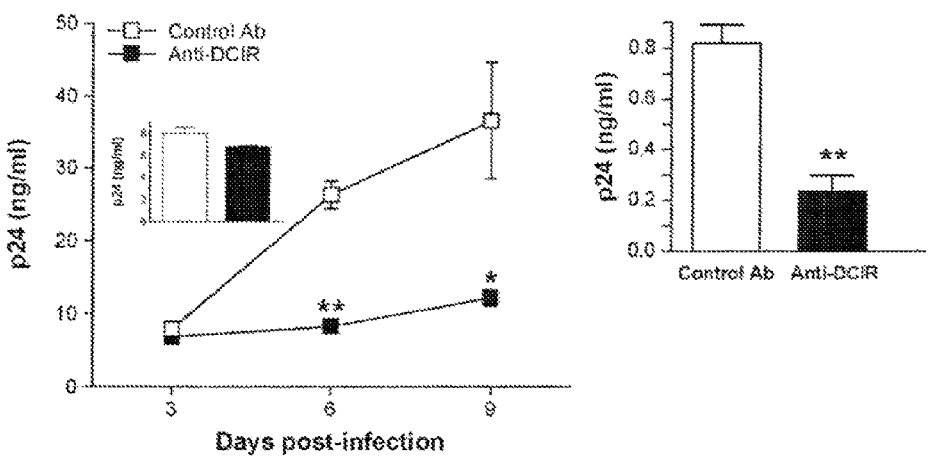

SEQ ID NO: 6

```
          10          20          30          40          50          60
MTSEITTYAEV RFKNEFKSSG INTASSAASK  ERTAPHKSNT GEPKLLCASL LIFFLLLAIS
    ITIM motif                                          Transmembrane domain
          70          80          90         100         110         120
FFIAFVIFFQ KYSQLLEKKT TKELVHTTLE  CVKKNMPVEE TAWSCCPKNW KSFSSNCYFI
         Neck domain                                              CRD domain
         130         140         150         160         170         180
STESASWQDS EKDCARMEAH LLVINTQEEQ  DFIFQNLQEE SAYFVGLSDP EGQRHWQWVD
         190         200         210         220         230         237
QTPYNESSTF WHPREPSDPN ERCVVLNFRK  SPKRWGWNDV NCLGPQRSVC EMMKIHL
         Blocking antibody                 Blocking antibody
         EPS motif = 195-197

ITIM    5-10
neck    66-99
CRD     113-237
EPS     187-202
COOH    223-237
```

Figure 9 siRNA were designed to recognize the following sequences :

ATTTAGGTGGTCTGTCA [SEQ ID NO : 11]

AAGGGAGGTCCATTAGAATTA [SEQ ID NO : 12]

DCIR sequence [SEQ ID NO : 1] :

TGTGATTCTCACTATACTGGTCCTGAGGGAAGGGCTCTGTGAACTGCGGTTTTTAGTTTTATTGTGGTTCTTAGTTGTCAATGAGACCCCTCTTGAGGATATGTGCCTATCTGGTG
CCTCTGCTCCCACTAGTTGAGTGAAAGGAAGGAGGTAATTTAGTGTTTTAAGAGATTGTTTTAAGAAACAGATTTTCTGAAGAAAGCAGAGC
TCTTCTTCCCATTATGACTTCGGAAATCACTTATGCTGAAGTGAGGTTGCCTCACGTGTTGTGCCTCACGTCTTGTGCCTATGTTGATATTTTCCAAAAATGAATTCAACACAGCCTCTTCCTGCAGCTTTCATTTTTCTTTGCTTTGTCATTTCAAAAATATTCTCAG
CACAAAAGTAATAATACCGGATCCCAAGCTGGTTCCCAAGCTGTCCTTTGTGCATACAACATTGGGCAATCCATTCTTTATTGCCCAAAGACAGCCTGTTGCCAAAGAATTGGAAGTCATTT
CTTCTTGAAAAAAGACTACACATTGGTTCATACAACATTGGGCAGTGTGTGGAGTCTGTGCAGACTGTGAAGACAGACTGAGACATTGGGCAGACAGCTCAGAGAGAGCAGAGATTTC
AGTTCCACTGCTACTTATTTCTACTGAATCAGATCTTGGCAGACATCTTGTGGGGCTCTGATTTTGTGGGGCTCTGTGATAACACTCAAGAGACGAGAGCAGAGATTCGG
ATCATCCAGAATCTGCAAGAGAATCTGCTTATTTGTGGGGGCTGCTTATTTGTGGGGCTCTCAGATCCAGGAGTGAGGTCAGAGACACCATGAATGACCATGCATTCCACATCGG
CATCCACGTGAGCCCAGTGATCCCAATGAGCGCTGCGTTGTGCTAAATCACCGGAATGATGTTAATTGTGTGGCCTCAAAGTCAGTTTTGT
GAGATGATGAAGAAGAATCCACTTATGAACTGAACATTCCCATGAACTGGTGGTTCGTGTACATTGACTGATTCACTTTTTCATTGAGCATTTATTGACGTATTGAGCATTTTTCATGTGCCAGAGCC
ATAGAATTTAGGTGGTCTGTCAACTATTCTACTGAGAGAACATGAGTCTCTCTTAAGATTATTTTATCTGGTTGCTAAAGAATTATTACCAATAAAATTATATGAGTGGTGTCCAAAAAAA
TGTACTGGAGGGCCCCATTGTGCACACATGGAGAGAACATGAGTCTCTCTTAAGATTATTTTATCTGGTTGCTAAAGAATTATTACCAATAAAATTATATGAGTGGTGTCCAAAAAAA
AAA

Figure 10

METHOD FOR INHIBITING DENDRITIC CELL IMMUNORECEPTOR (DCIR)-MEDIATED HUMAN IMMUNODEFICIENCY VIRUS INFECTION COMPRISING ADMINISTERING ANTI-DCIR ANTIBODIES

This U.S. patent application is a continuation of U.S. 12/457,673 filed Jun. 18, 2009 now abandoned which claims benefit of U.S. 61/129,343 filed Jun. 19, 2008 and benefit of Canadian application 2,633,246 filed Jun. 20, 2008, the entire content of each of these applications being incorporated herein by reference.

FIELD OF THE INVENTION

The present invention relates to the identification of therapeutic agents to prevent and/or control HIV infection. More particularly, the present invention relates to compounds and their use for impairing the interaction between a C-type lectin designated dendritic cell immunoreceptor (DCIR) and human immunodeficiency virus (HIV). These compounds may be particularly useful in the treatment or prevention of HIV infection.

BACKGROUND OF THE INVENTION

Dendritic cells (DCs) play a pivotal role in the establishment and dissemination of human immunodeficiency virus type 1 (HIV-1) infection as well as in the development of a virus-specific immune response. The involvement of this cell type in the overall pathogenesis of the disease was described soon after the discovery of this retrovirus, but its exact contribution remains elusive.

The mechanism by which HIV-1 is transmitted from the mucosa to $CD4^+$ T cells is not entirely understood. Three possibilities have been proposed to explain how mucosal DCs come in contact with HIV-1. The first proposes a selective transcytosis of R5-tropic virions through the mucosal cells. The second suggests that the initial transmission of R5 virions can occur by infection of mucosal epithelial cells via the galactosylceramide and/or CCR5 receptors. The third alternative promotes the idea that DCs present in the submucosal tissue capture HIV-1 particles with their dendrites. In all three pathways, the crucial events in both virus entry and transmission are the binding and capture of viruses by specific cell surface receptors.

It is now well established that internalization of HIV-1 into target cells requires the formation of a fusion pore resulting from a high-affinity interaction between envelope spike glycoproteins (i.e., gp120) and a complex consisting of the CD4 receptor and a seven-transmembrane coreceptor (e.g., CXCR4 or CCR5). However, it is becoming clear that the initial attachment step is more complex than first thought, since it is modulated by a number of interactions between the viral entity and the target cell surface. The most convincing example is the association between the gp120 oligosaccharides and different C-type lectin receptors, such as mannose receptor (CD206), langerin (CD207), and DC-specific intercellular adhesion molecule 3 (ICAM-3)-grabbing nonintegrin (DC-SIGN; also called CD209), which are all expressed on DCs. This association results in the capture of HIV-1 and its subsequent transmission to $CD4^+$ T cells, preferentially in a trans-infectious mode.

Following its capture by C-type lectin receptors, a virus particle is rapidly taken up into endolysosomal vacuoles, where it remains infectious for 1 to 3 days, which is approximately the time required for the migration of DCs to the draining lymph nodes. When these DCs encounter $CD4^+$ T cells, the internalized viruses rapidly relocate to the DC-T-cell contact zone, the local region between the two cell types where viruses concentrate, referred to as the virological synapse. Such a close encounter between cells and viruses leads to efficient transfer, subversion of the immune system, and virus production in both cell types, particularly in responder $CD4^+$ T lymphocytes. The reported low levels of CD4, CXCR4, and CCR5 on DCs are probably responsible for their weaker susceptibility to productive HIV-1 infection in vitro compared to that of $CD4^+$ T cells. Interestingly, a recent work has shown that HIV-1 transfer from DCs to $CD4^+$ T cells occurs in two distinct phases. In the initial transfer phase (i.e., early transfer) viruses located within endosomal compartments in DCs are transported to the DC-T-cell synapse as described above. This is followed by a second phase (i.e., late transfer) that is dependent on productive infection of DCs and eventual transfer of progeny virus to $CD4^+$ T cells.

Immature dendritic cells residing in the peripheral tissue such as the epithelial and subepithelial layer of the mucosa are considered the initial targets of HIV. HIV-infected immature dendritic cells then migrate to lymphoid organs and disseminate the virus in the body by either releasing newly synthesized virus or by transmitting the virus to $CD4^+$ T-cells in a trans-infectious mode.

Although C-type lectin such as DC-SIGN participates in the capture of HIV by dendritic cells, it seems that the attachment of HIV to DC-SIGN is not sufficient to allow infection of dendritic cells.

There is thus a need to identify other molecules involved in the early phase of HIV infection.

SUMMARY OF THE INVENTION

DCIR has been identified in 1999 by Bates et al. (Journal of Immunology, 163:p 1973-1983, 1999). But the role of DCIR has not yet been fully understood.

The present invention is based on the identification of the involvement of DCIR in the attachment of HIV, infection of dendritic cells and subsequent transmission of HIV from dendritic cells to $CD4^+$ T-cells.

As such, the present invention relates to the identification of therapeutic agents for the control of HIV infection. More particularly, the present invention relates to compounds and their use for impairing the interaction between a newly discovered HIV receptor named DCIR and HIV. These compounds may be particularly useful in the treatment or prevention of HIV infection. The present invention also includes pharmaceutical compositions and methods of treatment.

Also provided herein are assays and methods for identifying compounds which have the ability to impair or even to inhibit the interaction between HIV and DCIR, HIV infection of dendritic cells and/or dissemination of HIV by dendritic cells.

A person of skill in the art will understand that once an interaction between two entities is discovered, several types of assays (e.g., cell based and/or biochemical assays, etc.) may be carried out to identify compounds capable of impairing or inhibiting this interaction. Several libraries of molecules are commercially available and may be used to identify putative inhibitors.

The present invention thus provides in a first aspect thereof, compounds capable of inhibiting an interaction between HIV and DCIR. Such compounds includes, without limitation, small molecules, proteins or peptides, antibodies or antigen binding fragments thereof, nucleic acids, etc.

It has been shown herein that cells expressing DCIR at the their surface become more readily infected by HIV or transfer HIV particles to CD4+ cells in a more efficient manner.

As such, other aspect of the present invention also relates to compounds which may be capable of reducing DCIR cellular expression and/or DCIR cell surface expression.

BRIEF DESCRIPTION OF THE DRAWINGS

In the appended drawings:

In FIG. 4A the experiment was carried out in the presence or absence of efavirenz;

FIG. 5 right panel, are graphs illustrating virus production by HIV-infected IM-MDDC from two different donors which are treated with anti-DCIR antibodies or control antibodies. left panel: are graphs illustrating the results of co-culture experiments between HIV-infected IM-MDDC (treated with anti-DCIR antibodies or control antibodies) and autologous CD4+ T cells for two different donors;

FIG. 9 represents the amino acid sequence of DCIR (SEQ ID NO: 6), and;

FIG. 10 represents the nucleic acid sequence of DCIR (SEQ ID NO: 1) and the DCIR sequences (SEQ ID NOs: 11 and 12) that were targeted by DCIR-specific siRNAs according to the Examples.

DETAILED DESCRIPTION

Figure 1:
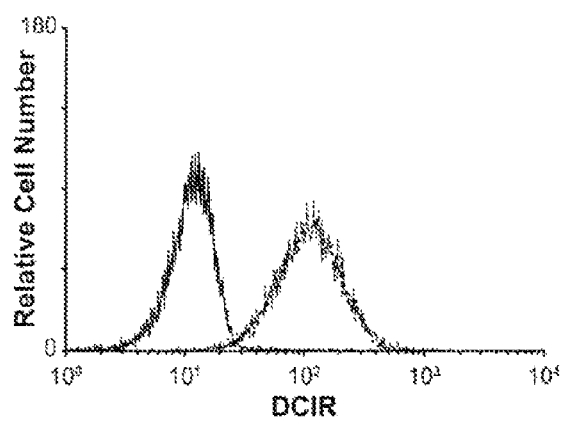
FIG. 1 illustrates DCIR expression as determined by flow cytometry analysis in immature-monocyte derived dendritic cells (IM-MDDC)

The present invention relates to the identification of therapeutic agents for HIV infection. More particularly, the present invention relates to compounds and their use for impairing the interaction between DCIR and HIV. These compounds may be particularly useful in the prevention and/or treatment of HIV infection.

As used herein the term "HIV" means human immunodeficiency virus and includes human immunodeficiency virus type-1 (HIV-1) and human immunodeficiency virus type-2 (HIV-2).

The present invention thus provides in a first aspect thereof, a compound capable of inhibiting an interaction between HIV and DCIR.

The compound may be, for example, a small molecule, an antibody or an antigen binding fragment thereof. Antibodies of the present invention include anti-DCIR antibodies or an antigen binding fragment thereof. Antibodies or antigen binding fragment which are particularly useful to carry out the present invention are those which are capable of specific binding to an extracellular region of DCIR (e.g. amino acids 69 to 237 of DCIR).

In accordance with the present invention, the antibody or antigen binding fragment may be capable of specific binding to a carboxy terminal region of DCIR.

In an exemplary embodiment of the invention, the antibody or antigen binding fragment may be capable of specific binding to a DCIR epitope comprising at least 5 amino acids of DCIR. More particularly, the antibody or antigen binding fragment may target an extracellular region of DCIR comprising at least 5 amino acids.

In another exemplary embodiment of the invention, the antibody or antigen binding fragment may be capable of specific binding to a DCIR epitope comprising for example, at least 5 consecutive amino acids of a region spanning amino acids 187 to 237 of DCIR. For example, the antibody or antigen binding fragment may be capable of specific binding to a DCIR epitope comprising, from 5 to 15 amino acids of LGPQRSVCEMMKIHL [SEQ ID NO:10] or comprising for example, from 5 to 16 amino acids of SSTFWHPREPSDPNER [SEQ ID NO:42] from 5 to 17 amino acids of RKSPKRWGWNDVNCLGP [SEQ ID NO:43]. Alternatively the antibody or antigen binding fragment may be capable of specific binding to a DCIR epitope comprising from 5 to 33 amino acids of IFFQKYSQLLEKKTTKELVHTTLECVKKNMPVE [SEQ ID NO:44].

In another exemplary embodiment of the present invention, the antibody or antigen binding fragment may be capable of competing with an antibody specific for an epitope which comprises for example, at least 5 amino acids of DCIR. More particularly, the antibody or antigen binding fragment may compete with an antibody targeting an extracellular region of DCIR comprising at least 5 amino acids.

In another exemplary embodiment of the present invention, the antibody or antigen binding fragment may be capable of competing with an antibody specific for an epitope which comprises for example, from 5 to 15 amino acids LGPQRSVCEMMKIHL [SEQ ID NO:10] for binding to DCIR.

In still another exemplary embodiment of the invention, the antibody or antigen binding fragment may be capable of competing with an antibody specific for an epitope comprising for example, from 5 to 16 amino acids of SSTFWHPREPSDPNER [SEQ ID NO:42].

Those of skill in the art will recognize that either polyclonal or monoclonal antibodies may possess the desired characteristics. These antibodies may come from various sources including, without limitation, from a mouse, a rabbit, a camel (Nanobodies®), etc.

The antigen binding fragment may be in the form of an Fab fragment; an F(ab')$_2$ fragment, and Fv fragment; CDRs, single chain antibodies etc.

More particularly, suitable antibody or antigen binding fragment of the present invention are those which are capable to impair and/or inhibit transmission of HIV from dendritic cells to CD4-positive T-cells. Alternatively, other suitable antibody or antigen binding fragments of the present invention are those which are capable of impairing or inhibiting infection of dendritic cells by HIV.

Four isotypes of DCIR exist naturally. The role of each isotype has not yet been deciphered. Nevertheless, substantial amino acid similarity (overlap) exists between each isotype.

The present invention applies to DCIR isotypes such as those described in SEQ ID NO.: 6, SEQ ID NO.:7, SEQ ID NO.:8 and SEQ ID NO.:9 but also to DCIR analogues, including synthetic analogues and orthologues from other species. For the purpose of the experimentations carried out herein, isotype 1 or a neck deleted variant were used.

Other aspects of the invention therefore relates to the use of a DCIR sequence selected from the group consisting of any one of SEQ ID NOs.:6 to 9, analogues or fragments thereof for the preparation of anti-DCIR antibodies or antigen binding fragments thereof for the inhibition of infection by HIV. The invention thus relates to the use of SEQ ID NOs.:6 to 9, analogues or fragments thereof in the preparation of a medicament for the treatment of HIV infection (e.g., reducing viral load in an individual).

The DCIR fragment used for generating such antibodies are preferably localized in the extracellular region of DCIR and more particularly in the carboxy terminal region of DCIR.

In an exemplary embodiment, the DCIR fragment may comprise at least 5 amino acids of an amino acid sequence selected from the group consisting of any one of SEQ ID NO.:6 to 9 or analogues of SEQ ID NO.:6 to 9.

In another exemplary embodiment the fragment may comprise, for example, from 5 to 15 amino acids of SEQ ID NO.: 10. In still another exemplary embodiment the fragment may comprise from 5 to 16 amino acids of SEQ ID NO.:42. In an additional embodiment of the invention, the fragment may comprise from 5 to 17 amino acids of SEQ ID NO.:43.

As used herein the term "analogue" or "analog" relates to mutants, chimeras, fusions, a polypeptide comprising at least one amino acid deletion, a polypeptide comprising at least one amino acid insertion or addition, a polypeptide comprising at least one amino acid substitutions, and any other type of modifications made relative to a given polypeptide.

An "analogue" is thus to be understood herein as a molecule having a biological activity and/or chemical structure similar to that of a polypeptide described herein. An "analogue" may have sequence similarity with that of an original sequence or a portion of an original sequence and may also have a modification of its structure as discussed herein. For example, an "analogue" may have at least 80% identity or at least 80% sequence similarity with an original sequence or a portion of an original sequence.

As used herein the term "at least 80% identity" means that the polypeptide has at least 80% or higher of its amino acid that are identical to an original (or reference) sequence. The term "at least 80% identity" also encompass, "at least 81% sequence identity", "at least 82% sequence identity", "at least 83% sequence identity", "at least 84% sequence identity", "at least 85% sequence identity", "at least 86% sequence identity", "at least 87% sequence identity", "at least 88% sequence identity", "at least 89% sequence identity", "at least 90% sequence identity", "at least 91% sequence identity", "at least 92% sequence identity", "at least 93% sequence identity", "at least 94% sequence identity", "at least 95% sequence identity", "at least 96% sequence identity", "at least 97% sequence identity", "at least 98% sequence identity", "at least 99% sequence identity" and "at least 100% sequence identity".

As used herein the term "at least 80% similarity" means that the polypeptide has at least 80% or higher of its amino acid that are either identical to an original (or reference) sequence and/or being conservative amino acid substitutions.

Example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word-length (W) of 11, an expectation (E) of 10, M=5, N=−4, and a comparison of both strands. For amino acid sequences, the BLASTP program uses as defaults a word-length (W) of 3, an expectation (E) of 10, and the BLOSUM62 scoring matrix (see Henikoff & Henikoff, Proc. Nat'l. Acad. Sci. USA 89:10915 (1989)).

In addition to calculating percent sequence identity, the BLAST algorithm also performs a statistical analysis of the similarity between two sequences (see, e.g., Karlin & Altschul, Proc. Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Based on the above, percent (%) amino acid sequence identity with respect to the polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity.

Percent (%) amino acid sequence similarity with respect to the polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and also considering conservative substitutions.

An "analogue" also encompass a polypeptide which may comprise one or more modification; for example, one or more modification in the amino acid sequence (e.g., an amino acid addition, deletion, insertion, substitution etc.), one or more modification in the backbone or side-chain of one or more amino acid, or an addition of a group or another molecule to one or more amino acids (side-chains or backbone).

Example of substitutions may be those, which are conservative (i.e., wherein a residue is replaced by another of the same general type or group) or when wanted, non-conservative (i.e., wherein a residue is replaced by an amino acid of another type). In addition, a non-naturally occurring amino acid may substitute for a naturally occurring amino acid (i.e., non-naturally occurring conservative amino acid substitution or a non-naturally occurring non-conservative amino acid substitution).

As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same type or group as that of the amino acid to be replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

Naturally occurring residues are often divided into groups based on common side chain properties:

It should be further noted that if the polypeptides are made synthetically, substitutions by amino acids, which are not naturally encoded by DNA (non-naturally occurring or unnatural amino acid) may also be made.
(1) hydrophobic: norleucine, methionine (Met), Alanine (Ala), Valine (Val), Leucine (Leu), Isoleucine (Ile)
(2) neutral hydrophilic: Cysteine (Cys), Serine (Ser), Threonine (Thr)
(3) acidic: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro); and aromatic: Tryptophan (Trp), Tyrosine (Tyr), Phenylalanine (Phe)

It should be further noted that if the polypeptides are made synthetically, substitutions by amino acids, which are not naturally encoded by DNA (non-naturally occurring or unnatural amino acid) may also be made.

A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide. Non-naturally occurring amino acids (residues) include also the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, norleucine, etc. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

Examples of substitutions identified as "conservative substitutions" are shown in Table 1. If such substitutions result in a change not desired, then other type of substitutions, denominated "exemplary substitutions" in Table 1, or as further described herein in reference to amino acid classes, are introduced and the products screened.

Non-conservative substitutions will entail exchanging a member of one of these classes for another.

TABLE 1

Exemplary amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Examples of Antibodies, Assays and Kits

Antibodies and antigen binding fragment that may specifically bind to DCIR and epitopes described herein as well as nucleic acids encoding such antibodies or antigen binding fragment are also encompassed by the present invention.

As used herein the term "antibody" means a monoclonal antibody, a polyclonal antibody, a single chain antibody, a chimeric antibody, a humanized antibody, a deimmunized antibody, an antigen-binding fragment, an Fab fragment; an F(ab')$_2$ fragment, and Fv fragment; CDRs, or a single-chain antibody comprising an antigen-binding fragment (e.g., a single chain Fv).

Peptides corresponding to desired DCIR epitopes may be made by any procedure known to one of skill in the art, for example, by using in vitro translation or chemical synthesis procedures or by introducing a suitable expression vector into cells. Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids.

Examples include serum albumins, keyhole limpet hemocyanin, ovalbumin, polylysine and the like. One of skill in the art may use available procedures and coupling reagents to link the desired peptide epitope to such a carrier. For example, coupling reagents may be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies may vary. The minimum size must be sufficient to provide an antigenic epitope that is specific to the protein or polypeptide. The maximum size is not critical unless it is desired to obtain antibodies to one particular epitope. Typically, antigenic peptides selected from the present proteins and polypeptides will range without limitation, from 5 to about 100 amino acids in length. More typically, however, such an antigenic peptide will be a maximum of about 50 amino acids in length, and preferably a maximum of about 30 amino acids. It is usually desirable to select a sequence of about 6, 7, 8, 9, 10, 11, 12, 13, 14 or 15 amino acids, up to about 20 or 25 amino acids (and any number therebetween).

As used herein the term "at least 5 amino acids" of DCIR includes "at least 6 amino acids", "at least 7 amino acids", "at least 8 amino acids", "at least 9 amino acids", "at least 10 amino acids" and so on up to the entire length of the protein (DCIR).

As used herein the term "comprising from 5 to 15" or "comprises from 5 to 15" is intended to include 5 amino acids of a sequence, 6 amino acids of a sequence, 7 amino acids of a sequence, 8 amino acids of a sequence, 9 amino acids of a sequence, 10 amino acids of a sequence, 11 amino acids of a sequence, 12 amino acids of a sequence, 13 amino acids of a sequence, 14 amino acids of a sequence and 15 amino acids of a sequence.

Amino acid sequences comprising useful epitopes may be identified in a number of ways. For example, preparing a series of short peptides that taken together span the entire protein sequence may be used to screen the entire protein sequence. One of skill in the art may routinely test a few large polypeptides for the presence of an epitope showing a desired reactivity and also test progressively smaller and overlapping fragments to identify a preferred epitope with the desired specificity and reactivity.

To obtain polyclonal antibodies, a selected animal may be immunized with a protein or polypeptide. Serum from the animal may be collected and treated according to known procedures. Polyclonal antibodies to the protein or polypeptide of interest may then be purified by affinity chromatography. Techniques for producing polyclonal antisera are well known in the art.

Monoclonal antibodies (mAbs) may be made by several procedures available to one of skill in the art, for example, by fusing antibody producing cells with immortalized cells and thereby making a hybridoma. The general methodology for fusion of antibody producing B cells to an immortal cell line is well within the grasp of one skilled in the art. Another example is the generation of mAbs from mRNA extracted from bone marrow and spleen cells of immunized animals using combinatorial antibody library technology.

Chimeric antibodies may include antibodies where some or all non-human constant domains have been replaced with human counterparts. This approach has the advantage that the antigen-binding site remains unaffected. However, significant amounts of non-human sequences may be present where variable domains are derived entirely from non-human antibodies.

Humanized antibodies may be constructed in which regions of a non-human mAb are replaced by their human counterparts. A preferred chimeric antibody is one that has amino acid sequences that comprise one or more complementarity determining regions (CDRs) of a non-human mAb that binds to a polypeptide of interest or to a portion thereof, grafted to human framework (FW) regions. Methods for producing such antibodies are well known in the art. Amino acid residues corresponding to CDRs and FWs are known to one of average skill in the art.

Antibodies of the invention also include human antibodies that are antibodies consisting essentially of human sequences. Human antibodies may be obtained from phage display libraries wherein combinations of human heavy and light chain variable domains are displayed on the surface of filamentous phage. Combinations of variable domains are typically displayed on filamentous phage in the form of Fab's or scFvs. The library may be screened for phage bearing combinations of variable domains having desired antigen-binding characteristics. Preferred variable domain combinations are characterized by high affinity for a polypeptide, or a portion thereof. Preferred variable domain combinations may also be characterized by high specificity for a polypeptide and little cross-reactivity to other related antigens. By screening from very large repertoires of antibody fragments, ($2-10 \times 10^{10}$) a good diversity of high affinity mAbs may be isolated, with many expected to have sub-nanomolar affinities for a desired polypeptide.

Alternatively, human antibodies may be obtained from transgenic animals into which un-rearranged human Ig gene segments have been introduced and in which the endogenous mouse Ig genes have been inactivated. Preferred transgenic animals contain very large contiguous Ig gene fragments that are over 1 Mb in size but human polypeptide-specific mAbs of moderate affinity may be raised from transgenic animals containing smaller gene loci. Transgenic animals capable of expressing only human Ig genes may also be used to raise polyclonal antiserum comprising antibodies solely of human origin.

Antibodies of the invention may include those for which binding characteristics have been improved by direct mutation or by methods of affinity maturation. Affinity and specificity may be modified or improved by mutating CDRs and screening for antigen binding sites having the desired characteristics. CDRs may be mutated in a variety of ways. One way is to randomize individual residues or combinations of residues so that in a population of otherwise identical antigen binding sites, all twenty amino acids may be found at particular positions. Alternatively, mutations may be induced over a range of CDR residues by error prone PCR methods. Phage display vectors containing heavy and light chain variable region gene may be propagated in mutator strains of *E. coli*. These methods of mutagenesis are illustrative of the many methods known to one of skill in the art.

The antibody of the present invention may further comprise a detectable label (reporter molecule) attached thereto.

There is provided also methods of producing antibodies able to specifically bind to the protein or peptide described, the method may comprise: immunizing a mammal with a suitable amount of the protein or peptide comprising a desired DCIR epitope;
  a) collecting the serum from the mammal; and
  b) isolating the polypeptide-specific antibodies from the serum of the mammal.

Methods of producing antibodies for the inhibition of HIV infection. encompass using (immunizing an animal with) a DCIR sequence selected from the group consisting of any one of SEQ ID NOs.:6 to 9, analogues or fragments thereof for preparing anti-DCIR antibodies In addition to their specificity, the antibodies may be characterized for their ability to interfere with HIV infection of dendritic cells or to interfere with the binding of HIV to DCIR using techniques described herein or other techniques known to a person of skill in the art. An anti-DCIR antibody which is capable of interfering with infection and/or binding of HIV to dendritic cells or DCIR is indicative of an antibody which may be useful in lowering HIV infection, dissemination and/or transmission. The antibodies or antigen binding fragments may also be tested for their capacity to interfere with transfer of HIV to $CD4^+$ T-cells.

The antibodies obtained by the means described herein may be useful for detecting DCIR in specific tissues, body fluid, culture medium, etc. The anti-DCIR antibodies (alone or in combination with other antibodies) may also be useful in isolating or detecting HIV infected DCIR expressing cells.

Kits containing anti-DCIR antibody(ies) are also encompassed by the present invention.

Nucleic Acid-based Compounds

It has also been shown herein that cells expressing DCIR at their surface become more readily infected by HIV or transfer HIV particles to adjacent CD4-positive cells in a more efficient manner.

As such, other aspect, the present invention also relates to compounds which may be capable of reducing DCIR cellular expression and/or DCIR cell surface expression.

Such compound may comprise, for example, an interfering RNA, an antisense oligonucleotide or any other type of nucleic acid capable of hybridizing with SEQ ID NO.:1 or RNA expressed therefrom. Desired nucleic acids are those which are able to lower expression of DCIR no matter the mechanism of action.

RNA expressed from SEQ ID NO.:1 includes RNA corresponding to any of SEQ ID NO.:2, SEQ ID NO.:3, SEQ ID NO.:4, SEQ ID NO.:5, analogues or fragments thereof. Exemplary embodiment of RNA includes messenger RNA or heterogeneous RNA.

In an exemplary embodiment of the invention, interfering RNA which are capable of binding to a sequence selected from the group consisting of any one of SEQ ID NO.:11 to 41. In a more particular embodiment, the interfering RNA may be chosen for their capacity to bind under high stringency conditions to a sequence selected amongst any one of SEQ ID NO. 11 to SEQ ID NO.:41.

In another exemplary embodiment, the invention encompasses antisense oligonucleotides which may be complementary to all or a portion of a messenger RNA having at least 80% identity with a sequence selected from the group consisting of any one of SEQ ID NO.: 2, SEQ ID NO.: 3, SEQ ID NO.: 4 and SEQ ID NO.: 5.

The present invention also relates to a method of generating a nucleic acid capable of inhibiting the expression of a DCIR protein or DCIR messenger RNA the method may comprise providing a nucleic acid having a sequence having at least 80% identity with SEQ ID NO.:1, complement or a fragment thereof.

In accordance with an embodiment of the invention, the fragment may be capable of inhibiting expression of a sequence having at least 80% sequence identity with a sequence selected from the group consisting of any one of SEQ ID NO.: 2 to 5.

Interfering RNA

In order to identify suitable siRNA, the following procedures may be performed.

A target site for siRNA may be found by scanning for AA dinucleotide sequences beginning with the AUG start codon of a transcript. The 3' adjacent 19 nucleotides of any AA dinucleotide sequence may be used for potential siRNA target sites. However, siRNAs with other 3' terminal dinucleotide overhangs have been shown to effectively induce RNAi. If desired, the target site may be modified by selection strategy to design siRNAs with other dinucleotide overhangs.

The following criteria may also help in the optimization of siRNA:

siRNAs with 30-50% GC content appears to be more active than those with a higher G/C content;

Since a 4-6 nucleotide poly(T) tract acts as a termination signal for RNA pol III, stretches of >4 T's or A's in the target sequence are preferably avoided when designing sequences to be expressed from an RNA pol III promoter;

Since some regions of mRNA may be either highly structured or bound by regulatory proteins, siRNA target sites are generally selected at different positions along the length of the gene sequence;

The siRNA sequence is preferably specific of the target. To that effect comparison of the potential target sites with nucleic acid database (human, mouse, rat, etc.) may allow to eliminate from consideration any target sequences with more than 16-17 contiguous base pairs of homology to other coding sequences;

Targeted regions on the cDNA sequence of a targeted gene are preferably located 50-100 nt downstream of the start codon (ATG);

siRNA sequence preferably correspond to exons, and;

A negative control siRNA with the same nucleotide composition as the test siRNA but which lacks significant sequence homology to the genome may also be included in an assay. This negative control siRNA may also preferably be compared to sequences database to eliminate any homology to other coding sequences.

Once the siRNA target site is selected, the appropriate sense and antisense oligonucleotides may be synthesized with RNA polymerase promoter in operative association therewith and RNA transcribed using suitable enzymes and reagents. The sense and antisense RNA are allowed to associate and may be delivered to the cell. Alternatively, the interfering RNA may be delivered to the cell in the form of a short hairpin RNA (shRNA) expressed from an expression system (e.g., a vector, a virus, etc.) having for example a mammalian promoter allowing its expression in mammalian cells.

Antisense Oligonucleotides

Researchers have expended considerable effort to overcome the problems of limited membrane permeability and rapid enzymatic degradation of antisense oligonucleotides. To this end, researchers have utilized a variety of techniques designed to increase membrane permeability and mitigate the enzymatic degradation of antisense oligonucleotides.

A detailed discussion of oligonucleotide design and synthesis is presented in Uhlmann et al. Chemical Renews 90:543-584 (1990), the disclosure of which is hereby incorporated by reference in its entirety.

A preferred approach that has been used to enhance membrane permeability and stability of oligonucleotides is the use of alkyl-for-O substituted and S-for-O substituted nucleotide analogues. In connection with the alkyl substituted oligonucleotides, one of the phosphate oxygen atoms that is not involved with the bridge between nucleotides is substituted with an alkyl group (particularly, methyl or ethyl). Similarly, in the S-substituted oligonucleotides (phosphorothioates), one of the phosphate oxygen atoms that is not involved in the bridge is substituted with a sulfur. In the alkyl substituted oligonucleotides, a negatively charged oxygen is replaced with a neutral and sterically undemanding alkyl group (particularly methyl). With S-substituted oligonucleotides, the negative charge on the non-bridge oxygen atoms is shared asymmetrically and located primarily on the sulfur.

While inhibition of mRNA translation is possible utilizing either antisense oligoribonucleotides or oligodeoxyribonucleotides, free oligoribonucleotides are more susceptible to enzymatic attack by ribonucleases than oligodeoxyribonucleotides. Hence, oligodeoxyribonucleotides have generally been preferred because, upon hybridization with particular mRNA, the resulting DNA-RNA hybrid duplex is a substrate for RNase H, which specifically attacks the RNA portion of DNA-RNA hybrid at the free 2'-OH. Degradation of the mRNA strand of the duplex releases the antisense oligodeoxynucleotide strand for hybridization with additional messages from the gene.

A variety of other modified oligonucleotides have been synthesized to overcome this problem. See Uhlmann et al., supra. 2'-O-methyloligoribonucleotides have been synthesized and reportedly are completely resistant to RNA- and DNA-specific nucleases. See Sproat et al. Nucleic Acids Res. 17:3373 (1989), the disclosure of which is hereby incorporated by reference in its entirety. Less specific nucleases, however, cleave the 2'-O-methyloligoribonucleotides with varying efficiencies. Further, the same group reported the synthesis of other, larger, 2'-O-allyl-substituted oligoribonucleotides. See Iribarren et al. Proc. Nat. Acad. Sci. U.S.A., 87:7747 (1990), the disclosure of which is hereby incorporated by reference in its entirety. The paper reports that 2'-O-(2-propylene)-oligoribonucleotides are more stable than 2'-O-methyloligoribonucleotides and show improved specific binding. A branched, five carbon allyl substituted oligoribonucleotide (2'-O-(3,3-dimethyl-2-butene)-oligoribonucleotide) also substantially improved the resistance of the oligonucleotide to nuclease digestion. However, such oligonucleotide showed a substantially reduced hybridization with complementary RNA sequences.

As used herein the term "sequence identity" with respect to nucleic acid sequence relates to (consecutive) nucleotides of a nucleic acid sequence with reference to an original nucleic acid sequence which when compared are the same or have a specified percentage of nucleotides which are the same.

The identity may be compared over a region or over the total sequence of a nucleic acid sequence. Thus, "identity" may be compared, for example, over a region of 10, 19, 20 nucleotides (and any number therebetween) and more preferably over a longer region or over the entire region of a nucleic acid sequence. It is to be understood herein that gaps of non-identical nucleotides may be found between identical nucleic acids regions (identical nucleotides). For example, a nucleic acid sequence may have 100% identity with another nucleic acid sequence over a portion thereof. However, when the entire sequence of both nucleic acid sequence is compared, the two nucleic acid sequence may have 50% of their overall (total) sequence identity to one another.

Percent identity may be determined, for example, with n algorithm GAP, BESTFIT, or FASTA in the Wisconsin Genetics Software Package Release 7.0, using default gap weights.

Nucleic acid sequences or portion thereof having at least 80% sequence identity with an original nucleic acid sequence are encompassed by the present invention. As used herein, the expression "at least 80% sequence identity" means that a desired nucleic acid may have 80% sequence identity of higher (up to 100%) in comparison with another nucleic acid sequence. Thus, nucleic acid sequences having at least 81%, 82%, 83%, 84%, 85%, 86%, 87%, 88%, 89%, 90%, 91%, 92%, 93%, 94%, 95%, 96%, 97%, 98%, 99% or 100%, identity including any fractions in between are encompassed by the present invention.

As used herein the terms "sequence complementarity" refers to (consecutive) nucleotides of a nucleic acid sequence which are complementary to a reference (original) nucleic acid sequence. The complementarity may be compared over a portion or over the total sequence of a nucleic acid sequence.

As mentioned herein, nucleic acid sequences or portion thereof having at least 80% sequence complementarity with an original nucleic acid are thus encompassed by the present invention.

As used herein, the expression "at least 80% sequence complementary" means that a desired nucleic acid may have 80% sequence complementary or higher (up to 100%) in comparison with another nucleic acid sequence. Thus, nucleic acid sequences having 83%, 92.6%, 95%, 100%, 88%, 97.2%, 99.9% complementary including any number in between or any fractions in between are encompassed by the present invention. It is to be understood herein that the expression "having at least X % sequence complementarity with SEQ ID NO.:Y" is used interchangeably with the expression "having at least X % identity with a complement of SEQ ID NO.:Y".

As used herein the term "nucleic acid" generally refers to any polyribonucleotide or polydeoxyribo-nucleotide, which may be unmodified RNA or DNA, or modified RNA or DNA. "Nucleic acid" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "nucleic acid" may include triple-stranded regions comprising RNA or DNA or both RNA and DNA. The term nucleic acid also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus "nucleic acid" embraces chemically, enzymatically or metabolically modified forms of nucleic acid as typically found or not in nature, as well as the chemical forms of DNA and RNA characteristic of viruses and cells. "Nucleic acid" includes but is not limited to linear and end-closed molecules. "Nucleic acid" also embraces relatively short sequence, often referred to as oligonucleotides.

As known in the art, antisense oligonucleotides are often unstable or have limited membrane permeability. Therefore, the present invention encompass antisense oligonucleotides which comprise nucleotide analogues. Exemplary embodiment of nucleotide analogues are known in the art. A few examples of nucleotide analogues are however provided herein.

Suitable antisenses, interfering RNAs or other nucleic acid-based therapeutics are those which are capable of inhibiting transmission of HIV from dendritic cells to CD4-positive cells (e.g. CD4-positive T cells). Alternatively, other suitable antisenses, interfering RNAs or other nucleic acid-based therapeutics are those which are capable of impairing or inhibiting infection of dendritic cells by HIV or transmission of HIV from dendritic cells to CD4$^+$ cells.

It is to be understood herein that when the compound of the present invention comprises a nucleic acid (e.g., interfering RNA, antisenses, etc), such compound is designed to be preferably capable of hybridizing to a desired sequence under high stringency conditions. In an exemplary embodiment, the nucleic acids comprising one or two mismatches will usually bind to a complement almost as efficiently as a nucleic acid having no mismatches. As such, nucleic acid having one or two mismatches are encompassed by the present invention "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In addition to exemplary methods described herein, compounds useful for impairing or inhibiting HIV infection of DCIR expressing cells may also be identified by a method which may comprise contacting a test compound with a cell expressing DCIR and measuring HIV replication or transmission. In that instance, a diminution of HIV replication or transmission in the presence of the test compound may be indicative of a compound capable of reducing HIV infection of DCIR expressing cells or HIV dissemination by DCIR expressing cells.

Still other aspects of the invention relates to the use of a sequence having at least 80% sequence identity with SEQ ID NO.:1, a SEQ ID NO.:1 complement or a fragment thereof for generating a nucleic acid capable of inhibiting the expression of a DCIR protein or DCIR messenger RNA and more particularly for impairing HIV infection. The invention thus encompasses the use of a sequence having at least 80% sequence identity with SEQ ID NO.:1, a SEQ ID NO.:1 complement or a fragment thereof in the preparation of a medicament for the treatment of HIV infection (e.g., reducing viral load in an individual).

In accordance with the present invention, the SEQ ID NO.:1 fragment or complement thereof may be capable of inhibiting expression of a sequence having at least 80% identity with a sequence selected from the group consisting of any one of SEQ ID NO.: 2 to 5.

Assays and Methods

As used herein the term "dissemination" may include transmission of HIV from infected cells to non-infected cells.

Also provided herein are assays for identifying compounds which have the ability to impair or even to inhibit the interaction between HIV and DCIR, HIV infection of DCIR expressing cells and/or HIV dissemination by DCIR expressing cells.

A person of skill in the art will understand that once an interaction between two binding partners is discovered, several types of assays (e.g., cell based and/or biochemical assays) may be carried out to identify compounds capable of impairing or inhibiting this interaction. Several libraries of molecules are commercially available and may be used to identify putative inhibitors.

In an exemplary embodiment of the invention, a suitable compound may be identified by a method which may comprise contacting a test compound with a cell expressing DCIR and measuring HIV binding to DCIR. A diminution of binding in the presence of the test compound may thus be indicative of a compound capable of inhibiting the interaction between HIV and DCIR.

The present invention also relates in an additional aspect thereof to a method for identifying a compound which is capable of inhibiting an interaction between HIV and DCIR. The method may comprise contacting a test compound with a preparation comprising DCIR or a cell expressing DCIR and measuring HIV binding to DCIR or to the cell. A diminution of binding in the presence of the test compound may be indicative of a compound capable of inhibiting the interaction between HIV and DCIR.

Test compounds include an antibody or antigen binding fragment thereof, a protein or peptide, a small molecule etc.

The screening assay may also be carried out using recombinant proteins, e.g., gp120 and DCIR or recombinant DCIR with a preparation containing HIV or HIV-like particles.

In a further aspect the present invention relates to a method for identifying a compound that reduces HIV infection of DCIR expressing cells or HIV dissemination by DCIR expressing cells. The method may comprise contacting a test compound with a cell expressing DCIR and measuring HIV replication (e.g., amount of virus produced) or HIV transmission (e.g. to $CD4^+$ T-cells). A diminution of HIV replication or transmission in the presence of the test compound may be indicative of a compound capable of reducing HIV infection of DCIR expressing cells or HIV dissemination by DCIR expressing cells.

The cell used in the screening method may preferably carry a CD4 receptor. The cell may also preferably carry suitable HIV co-receptor(s).

In accordance with an embodiment of the invention, the DCIR expressing cell may be a CD4-positive cell. In accordance with a further embodiment of the invention, the DCIR expressing cell may be a CCR5-positive cell. In accordance with yet a further embodiment of the invention, the DCIR expressing cell may be a CXCR4-positive cell.

As described herein dendritic cells are suitable for screening for HIV inhibitors. The dendritic cell may be an immature dendritic cell.

Exemplary compounds that may be used in such methods includes without limitation, interfering RNAs, antisense RNAs, ribozymes, deoxyribozymes, proteins or peptides, antibodies or antibody fragments or small molecules.

Pharmaceutical Compositions and Methods for Impairing HIV Infection

Other aspects of the invention relate to a pharmaceutical composition for reducing HIV infection in a mammal. The composition may comprise, for example, a compound capable of inhibiting the interaction between HIV and DCIR and a pharmaceutically acceptable carrier. Alternatively, the composition may comprise, for example, a compound capable of reducing HIV infection of DCIR expressing cells or HIV dissemination by DCIR expressing cells and a pharmaceutically acceptable carrier.

In an exemplary embodiment of the invention, compounds comprising an anti-DCIR antibody or an antigen binding fragment thereof may be included in the pharmaceutical composition.

In another exemplary embodiment of the invention, compounds comprising of an interfering RNA or an antisense capable of hybridizing to a sequence selected from the group consisting of any one of SEQ ID NO.: 2, SEQ ID NO.:3, SEQ ID NO.:4, SEQ ID NO.:5 and analogues thereof may be included in the pharmaceutical composition.

In an additional aspect, the present invention relates to a method for treating an individual in need, e.g., an individual having an HIV infection (having an HIV related disorder (e.g., AIDS)) or susceptible of having an HIV infection (HIV related disorder (e.g., AIDS)).

In accordance with the present invention, the method may comprise administering to a mammal a compound capable of impairing an interaction between HIV and DCIR, a compound capable of reducing DCIR expression, a compound capable of reducing DCIR cell surface expression, a compound capable of reducing HIV infection of DCIR-expressing cells or HIV dissemination by DCIR-expressing cells.

As mentioned herein methods of the present invention include administering an anti-DCIR antibody or an antigen binding fragment thereof.

Suitable antibody or antigen binding fragment includes those which may be capable of specific binding to an extracellular region of DCIR. In an embodiment of the invention, antibody or antigen binding fragment encompassed by the present invention are those which are capable of specific binding to a carboxy terminal region of DCIR and are administered to an individual in need.

In an exemplary embodiment of the invention, antibody or antigen binding fragments which may be capable of specific binding to a DCIR epitope comprising for example from 5 to 15 amino acids of SEQ ID NO.:10, from 5 to 16 amino acids of SEQ ID NO.:42 or from 5 to 17 amino acids of SEQ ID NO.:43 may be administered to an individual in need.

In a further exemplary embodiment of the invention, antibody or antigen binding fragments which are capable of competing with an antibody for the binding to an epitope comprising from 5 to 15 amino acids of SEQ ID NO.:10, for the binding to an epitope comprising from 5 to 16 amino acids of SEQ ID NO.:42 or for the binding to an epitope comprising from 5 to 17 amino acids of SEQ ID NO.:43 may be administered to an individual in need.

Suitable epitopes (i.e., conjugated with a carrier or not) for generating an antibody or antigen binding fragment capable of inhibiting the interaction between DCIR and HIV-1 thus include an amino acid sequence of at least 5 amino acids of the extracellular region of DCIR (e.g. amino acids 69 to 237 of DCIR (with reference to isotype-1). An exemplary embodiment of such epitope includes for example, an amino acid sequence of at least 5 amino acids comprised between amino acids 187-237 of DCIR (with reference to isotype-1). More specific embodiments of useful epitopes include an amino acid sequence comprising or consisting of 5 to 15 amino acids of SEQ ID NO.:10, from 5 to 16 amino acids of SEQ ID NO.:42 or from 5 to 17 amino acids of SEQ ID NO.:43.

Methods of the present invention also include administering a compound which is capable of hybridizing with a nucleic acid encoding DCIR or with a complement thereof. Such compound may thus reduce expression of DCIR by mechanism involving RNA (e.g., mRNA) degradation or an impairment in RNA transcription or mRNA translation or else.

In an exemplary embodiment of the invention, a compound comprising an antisense nucleic acid capable of hybridizing to a DCIR mRNA expressed from a nucleic acid sequence having at least 80% sequence identity with SEQ ID NO.:1 may be administered to an individual in need. In a specific embodiment the antisense nucleic acid may be capable of hybridizing to a DCIR mRNA expressed from SEQ ID NO.:1.

In another exemplary embodiment of the invention, a compound which comprises an interfering RNA capable of hybridizing to a nucleic acid sequence having at least 80% identity with a sequence selected from the group consisting of any one of SEQ ID NOs.:2 to 5 may be administered to an individual in need. Suitable interfering RNA are those which are capable of hybridizing to a sequence selected from the group consisting of any one of SEQ ID NOs.:11 to 41.

In additional aspects, the present invention relates to the use of a compound described herein in the preparation of a medicament for the treatment of HIV infection or AIDS.

In yet additional aspects, the present invention relates to the use of a compound described herein in the treatment of HIV infection or AIDS.

Other objects, features, advantages, and aspects of the present invention will become apparent to those skilled in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

EXAMPLE SECTION

Material and Methods

Reagents: Recombinant human interleukin-2 (rhIL-2) and efavirenz (EFV) were obtained from the AIDS Repository Reagent Program (Germantown, Md.). IL-4 was purchased from R&D systems (Minneapolis, Minn.) whereas granulocyte macrophage-colony stimulating factor (GM-CSF) was a generous gift from Cangene (Winnipeg, MB). The culture medium consisted of RPMI-1640 supplemented with 10% fetal bovine serum (FBS), penicillin G (100 U/ml), streptomycin (100 U/ml), primocine (Amaxa Biosystems, Gaithersburg, Md.) and glutamine (2 mM), which were all purchased from Wisent (St-Bruno, QC).

Antibodies: The phycoerithrin (PE)-labeled anti-DCIR monoclonal antibody (Ab) (clone 216110) was purchased from R&D systems. A polyclonal anti-DCIR was produced in rabbits following immunisation with a peptide called 27P4 corresponding to the COOH-terminal domain of DCIR and more precisely to a region of DCIR spanning amino acids 223 to 237 (i.e. LGPQRSVCEMMKIHL [SEQ ID NO:10]) 1. Another antibody recognizing the EPS region of DCIR has been used herein. This antibody is directed against amino acids 187 to 202 of DCIR (i.e., SSTFWHPREPSDPNER; [SEQ ID NO:42]). The polyclonal anti-DCIR was purified using mAbTrap protein G affinity columns according to the manufacturer's instructions (Amersham Pharmacia Biotech, Piscataway, N.J.). PE-conjugated donkey anti-rabbit immunoglobulin G (IgG) was purchased from Jackson ImmunoResearch Laboratories (West Grove, Pa.). Hybridomas producing 183-H12-5C and 31-90-25, two Abs recognizing different epitopes of the HIV-1 major viral core protein p24, were supplied by the AIDS Repository Reagent Program and ATCC, respectively. Abs obtained from these hybridoma cell lines were also purified by using mAbTrap protein G affinity columns.

Cells: DC were generated from purified human monocytes (i.e. CD14$^+$ cells). Briefly, peripheral blood was obtained from normal healthy donors and peripheral blood mononuclear cells (PBMCs) were prepared by centrifugation on a Ficoll-Hypaque density gradient. Next, CD14$^+$ cells were isolated from fresh PBMCs by using a monocyte positive selection kit according to the manufacturer's instructions (MACS CD14 micro beads, STEMCell Technologies, Vancouver, BC) as described previously[2]. To generate immature monocyte-derived dendritic cells (IM-MDDC), purified monocytes were cultured in complete culture medium that was supplemented every other day with GM-CSF (1,000 U/ml) and IL-4 (200 U/ml) for 7 days. Autologous CD4$^+$ T cells were isolated using a negative selection kit according to the manufacturer's instructions (STEMCell Technologies). These cells were activated with phytohemagglutinin (PHA) (1 μg/ml) and maintained in complete culture medium supplemented with rhIL-2 (30 U/ml) at a density of $2 \times 10^6$ cells/ml. The percentage of cells expressing the surface markers CD3 and CD19 was evaluated to assess contamination with T and B cells, respectively. Experiments were performed with cell preparations that contained a minimal amount of contaminants (i.e. DC: purity >95%; CD4$^+$ T cells: purity >98%). Raji-CD4 is a B-cell line carrying the Epstein-Barr virus that has been rendered susceptible to HIV-1 infection by stable transfection with a cDNA encoding human CD4. These cells were cultured in RPMI-1640 medium supplemented with 10% FBS along with 1 mg/mL of the selective agent G418 (GIBCO-BRL, Gaithersburg, Md.). Human embryonic kidney 293T cells were cultured in Dulbecco's modified Eagle's medium supplemented with 10% FBS.

Flow cytometric analysis: Cell surface expression of DCIR was monitored by flow cytometric analysis with a flow cytometry apparatus (Epics ELITE ESP, Coulter Electronics, Burlington, ON). Before staining, cells were incubated for 15 min at 4° C. with 10% pooled human sera to block nonspecific binding sites and washed once with phosphate buffered saline (PBS) supplemented with 0.5% bovine serum albumin (BSA). Next, cells were incubated for 45 min at 4° C. with anti-DCIR (0.25 μg) monoclonal Ab and then washed twice with PBS and 0.5% BSA. Non-specific staining was determined by using an isotype-matched irrelevant control Ab. After two final washes with PBS, cells were fixed in 2% paraformaldehyde and analyzed.

Production of virus stocks: Virions were initially produced upon transient transfection of human embryonic kidney 293T cells as previously described[3]. The infectious molecular clones used in this study included pNL4-3balenv (R5-tropic) and pNL4-3 (X4-tropic). The pNL4-3balenv vector (provided by R. Pomerantz, Thomas Jefferson University, Philadelphia, Pa.) was generated by replacing the env gene of the T-tropic HIV-1 strain, NL4-3, with that of the macrophage-tropic HIV-1 Bal strain, thus resulting in an infectious molecular clone with macrophage-tropic properties[4]. Stocks of NL4-3balenv were made upon acute infection of PBMCs that were stimulated initially with PHA-L and maintained in culture medium containing rhIL-2. The virus-containing supernatants were harvested at day 7 post-infection, filtered through a 0.22-μm cellulose acetate syringe filter, ultracentrifugated and normalized for virion content using a sensitive in-house double-antibody sandwich enzyme-linked immunosorbent assay (ELISA) specific for the viral p24 protein. In this test, the 183-H12-5C and 31-90-25 Abs are used in combination to quantify p24 levels[5]. Preparations of NL4-3 were produced by infecting Raji-CD4. Briefly, Raji-CD4 cells ($5 \times 10^6$ cells) were inoculated with NL4-3 (at a ratio of 1 ng of p24 per $1 \times 10^5$ cells) for 2 h at 37° C. Cells were then washed extensively to eliminate uninternalized virions and maintained in culture for 6 days.

Nucleofection: The Amaxa Cell Line Nucleofector Kit V (Amaxa GmbH, Cologne, Germany) was used to achieve transient transfection of DCIR into Raji-CD4 (program M-13). Briefly, Raji-CD4 cells ($10 \times 10^6$ cells) were nucleofected with pBK-CMV-DCIR or pBK-CMV-DCIRΔneck (2.5 μg for each plasmid per $10 \times 10^6$ cells). These vectors were constructed by subcloning the cDNA coding for full length human DCIR or a neck-deleted version of DCIR (i.e. DCIRΔneck) into the pBK-CMV vector (Stratagene) as a KpnI-Xho fragment. These plasmids were purified using an EndoFree plasmid maxi kit (Qiagen, Mississauga, ON) to obtain DNA of high quality for nucleofection. Raji-CD4 cells were incubated for 5 hrs in RPMI-1640 medium supplemented with 20% FBS prior to nucleofection.

Gene silencing of DCIR with siRNAs: Small interfering RNAs (siRNAs) either specific (i.e. 5'-ATTTAGGTGGTCT-GTCA-3'; [SEQ ID NO:11]) or non-specific for DCIR (i.e. 5'-AATTCTCCGAAGGTGTCACGT-3'; [SEQ ID NO:45]) were obtained from Qiagen and dissolved in an appropriate buffer. The studied siRNAs were subsequently tested in IM-MDDC as previously described 2. Control cells were treated with either Oligofectamine alone or Oligofectamine and non-specific siRNAs. Forty hours following transfection, a virus transfer test was carried out as described below. The efficiency of DCIR silencing with the tested siRNA was monitored by flow cytometry.

HIV-1 transfer assay: IM-MDDC ($10^5$ cells in 100 μl) transfected either with the above listed siRNAs or pre-incubated with polyclonal anti-DCIR (10 μg/$1.5 \times 10^5$ cells) were exposed to HIV-1 (10 ng of p24) for 60 min at 37° C. Next, the virus-cell mixture was washed three times with PBS to remove unadsorbed virions. In some experiments, cells were also treated with the anti-HIV-1 drug EFV (efavirenz) (50 μM). Finally, IM-MDDC were co-cultured with autologous activated CD4$^+$ T lymphocytes at a 1:3 ratio in complete RPMI-1640 medium supplemented with IL-2 (30 U/ml) in 96-well plates in a final volume of 200 μl. At day 2, virus production was estimated by measuring p24 levels in cell-free culture supernatants by ELISA.

HIV-1 infection of IM-MDDC: IM-MDDC ($2\times10^5$ cells in a final volume of 100 µl) either transfected with the studied siRNAs or pre-incubated with the above mentioned polyclonal anti-DCIR were exposed to HIV-1 (20 ng of p24) for 2 hr at 37° C. After three washes with PBS, cells were maintained in complete RPMI-1640 culture medium supplemented with GM-CSF (1,000 U/ml) and IL-4 (200 U/ml) in 96-well plates in a final volume of 200 µl. Every 3 days and for a period lasting 9 days, half of the medium was removed and kept frozen at −20° C. until assayed. Virus production was estimated by measuring p24 levels in culture supernatants by ELISA. Note that in all experiments using the polyclonal anti-DCIR, DC were pre-treated with 10% of pooled human sera to avoid non-specific reactivity with Fc receptors.

Virus binding and infection assays in Raji-CD4: The role played by DCIR as a putative attachment factor for HIV-1 was assessed using a virus binding test. In brief, Raji-CD4, either negative (i.e. parental cell line) or positive for DCIR ($3\times10^6$ cells), were incubated with NL4-3 (300 ng of p24) for 60 min at 37° C. Next, the virus-cell mixture was washed three times with PBS to remove unbound virus and resuspended in PBS containing 1% BSA. The p24 content was determined. Susceptibility of the studied Raji-CD4 cells to HIV-1 infection was assessed by initially exposing DCIR-negative and DCIR-positive Raji-CD4 ($1.5\times10^5$ cells) to NL4-3 (1.5 ng of p24) for 2 hr at 37° C. Thereafter, cells were washed three times with PBS to remove non-specifically bound virions and were maintained in culture in 48-well plates in a final volume of 400 µl. Every 3 days post-infection and for a period lasting 9 days, half of the medium was removed from each well and kept frozen at −20° C. until assayed. Virus production was estimated by measuring p24 levels in cell-free culture supernatants.

Expression of DCIR on activated and resting CD4+ T cells: Briefly, peripheral blood was obtained from normal healthy donors or from aviremic patients and peripheral blood mononuclear cells (PBMCs) were prepared by centrifugation on a Ficoll-Hypaque density gradient. CD4+ T cells were isolated using a negative selection kit according as described above. These cells were maintained in complete culture medium supplemented with PHA-L/rhIL-2 (1 µg/ml and 30 U/ml respectively) for activated CD4+ T cells and without for resting CD4+ T cells at a density of $2\times10^6$ cells/ml. Before stimulation with $H_2O_2$ (30 µM for 16 hrs) cells were resuspended at $1\times10^6$ cells/ml in RPMI. Expression of DCIR is evaluated by cytofluorometry as described above.

Statistical analysis: Statistical analyses were carried out according to the methods outlined in Zar[6]. Means were compared using either the Student's t test or a single factor ANOVA followed by Dunnett's multiple comparison when more than two means were considered. P values of less than 0.05 were deemed statistically significant. Calculations were performed with the GraphPad Prism software.

Example 1

DCIR is Expressed on IM-MDDC

A previous study has demonstrated that DCIR is expressed by all circulating CD14+ monocytes, in DC derived from CD34+ cord blood progenitors as well as on the surface of DC generated in vitro upon culturing blood monocytes with GM-CSF and IL-4 (i.e. immature monocyte-derived DC or IM-MDDC)[7]. This last observation is of high importance because IM-MDDC are routinely used as an experimental cell system to study characteristics of mucosal myeloid DC and to define the complexity of interactions between DC and HIV-1[8]. To confirm that DCIR expression is maintained in IM-MDDC, cell surface expression of DCIR was determined by immunofluorescence staining and flow cytometric analysis.

Purified monocytes were cultured with GM-CSF and IL-4 for 7 days to derive IM-MDDC. DCIR expression was determined by flow cytometry analysis after staining with a commercial PE-conjugated anti-DCIR monoclonal Ab. Expression of DCIR is shown in FIG. 1 as a dotted line whereas the continuous line represents staining obtained with an isotype-matched irrelevant control Ab. Results shown are representative of seven independent experiments.

Data depicted in FIG. 1 indicate that DCIR is strongly expressed after culturing purified monocytes for 7 days with GM-CSF and IL-4, a treatment known to induce differentiation of monocytes into IM-MDDC.

Example 2

Role of DCIR in HIV-1 Uptake by IM-MDDC and Infection-siRNA Studies

In order to evaluate the potential role of DCIR in HIV infection, we used a first strategy, namely RNA interference (i.e. small interfering RNA or siRNA) to reduce DCIR expression in IM-MDDC. For the virus transfer assay, IM-MDDC were intentionally exposed to low doses of virions to better reflect the events occurring during mucosal transmission in vivo. Moreover, all virus stocks used in transmission assays were produced upon acute infection of primary human cells (i.e. PBMCs) to more closely parallel the natural microenvironment.

We thus employed RNA interference to reduce DCIR expression in IM-MDDC and analyzed the possible effect on HIV-1 transfer. IM-MDDC were either left untreated (control), transfected with a control siRNA [SEQ ID NO:45], or transfected with a DCIR-specific siRNA [SEQ ID NO:11]. After 40 hrs, flow cytometry analysis of DCIR was performed using a combination of PE-labelled anti-DCIR and isotype-matched control Ab. Data shown correspond to a single experiment representative of seven independent experiments.

Figure 2:
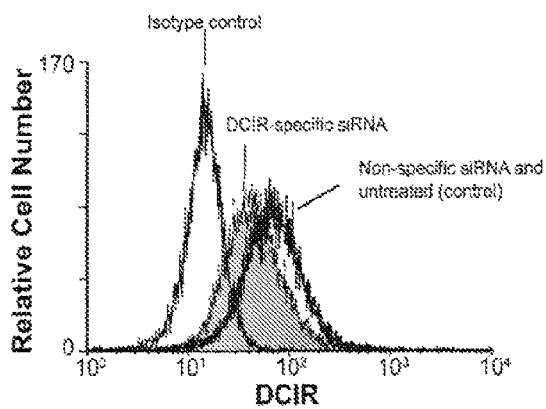
FIG. 2 illustrates DCIR expression in IM-MDDC either left untreated (control), transfected with a control siRNA, or transfected with a DCIR-specific siRNA.

A ~30% decrease in surface expression of DCIR in IM-MDDC was observed following the use of DCIR-specific siRNA (FIG. 2). It should be noted that DC-SIGN expression was not affected by DCIR-specific siRNA and cells viability was minimally affected upon siRNA treatment (data not shown).

Figure 3:
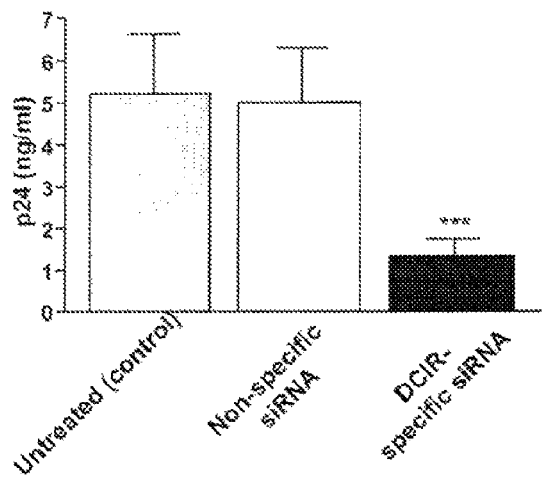
FIG. 3 is an histogram illustrating the results of co-culture experiments between HIV-infected IM-MDDC (untreated or treated with specific or unspecific siRNA) and autologous CD4+ T cells.

We next evaluated the transfer of HIV to autologous CD4+ T cells. To that effect, IM-MDDC ($1\times10^6$ cells) were treated with Oligofectamine and then either left untreated (control) or exposed to a non-specific siRNA and a DCIR-specific siRNA. Next, cells ($1\times10^5$) were pulsed with NL4-3balenv (10 ng of p24) for 60 min at 37° C. After three washes with PBS to eliminate unbound virus, IM-MDDC were co-cultured with autologous CD4+ T cells at a 1:3 ratio. Cell-free culture supernatants were collected at day 2 following initiation of the co-culture and analyzed for the p24 content. Data shown in FIG. 3 represent the means±SD of triplicate samples from three combined independent experiments. Asterisks denote statistically significant data (***, P<0.001).

Interestingly, transfer of HIV-1 was reduced significantly when IM-MDDC were transfected with DCIR-specific siRNA but not with a non-specific control siRNA (FIG. 3).

Similar observations were made when using another DCIR-specific siRNA [SEQ ID NO:12] (data not shown).

Example 3

DCIR is Involved in Trans- and Cis-infection Pathways

Previously published data demonstrated that HIV-1 is transferred from DC to CD4+ T cells through both trans- and cis-infection pathways[9]. Experiments were therefore carried out to define whether DCIR can contribute to HIV-1 dissemination via trans- and/or cis-infection processes. To solve this issue, virus transfer studies were performed using IM-MDDC that were initially transfected with the DCIR-specific siRNA and also treated with EFV, a non-nucleoside reverse transcriptase inhibitor. This antiretroviral compound hampers the late transfer (i.e. de novo virus production by IM-MDDC or cis-infection pathway) without affecting the early transfer mode (i.e. trans-infection pathway).

Figure 4:
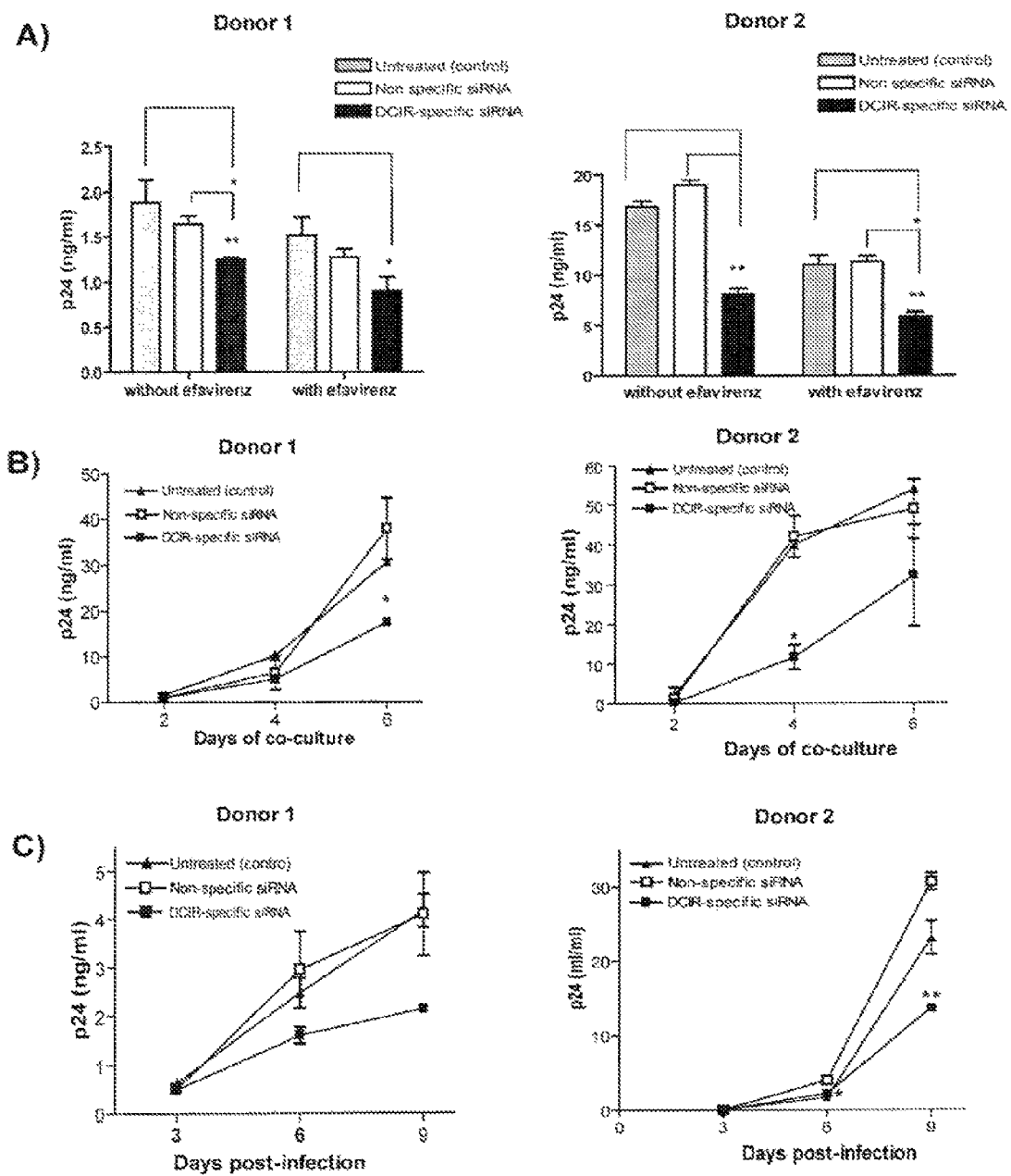
FIGS. 4A, 4B and 4C are graphs illustrating the results of co-culture experiments between HIV-infected IM-MDDC from two different donors (untreated or treated with specific or unspecific siRNA) and autologous CD4+ T cells.

In FIG. 4A, IM-MDDC ($1\times10^6$ cells) were treated with Oligofectamine and then either left untreated (control) or exposed to a non-specific siRNA and a DCIR-specific siRNA. Next, cells were either left untreated or treated with EFV. IM-MDDC ($2\times10^5$ cells) were pulsed with NL4-3balenv (20 ng of p24) for 60 min at 37° C. After three washes with PBS to eliminate unbound virus, IM-MDDC were co-cultured with autologous CD4+ T cells at a 1:3 ratio. Cell-free culture supernatants were collected at day 2 following initiation of the co-culture and analyzed for the p24 content. Data shown represent the means±SD of triplicate samples from two different donors and are representative of four separate donors. Asterisks denote statistically significant data (*, $P<0.05$, **, $P<0.01$). Results illustrated in FIG. 4A demonstrate that the use of the DCIR-specific siRNA led to a reduction in virus transfer corresponding to an average decrease of 30% in absence of EFV compared to an average diminution of 40% in cells treated with EFV. Such a small increment in the reduction of HIV-1 transfer by EFV suggests that DCIR contributes primarily to the early transfer phase (i.e. trans-infection pathway) with a small effect on the late transfer (i.e. cis-infection pathway).

The possible involvement of DCIR in the cis-infection mode was investigated further because of the limited effect of EFV on HIV-1 propagation. To this end, IM-MDDC treated with the DCIR-specific siRNA were first pulsed with HIV-1 and cultured for 4 days before initiating a co-culture with autologous CD4+ T cells. This experimental setup was prompted by the previous demonstration that, in IM-MDDC, most endosome-associated virus, which is responsible for the early transfer, is degraded within 24 to 48 hours[9,10].

In FIG. 4B, IM-MDDC were treated with Oligofectamine and then either left untreated (control) or exposed to a non-specific siRNA and a DCIR-specific siRNA. Cells ($2\times10^5$) were pulsed with NL4-3balenv (20 ng of p24) for 60 min at 37° C. After three washes with PBS to eliminate unbound virus, IM-MDDC were maintained in culture for 4 days. Finally, IM-MDDC were co-cultured with autologous CD4+ T cells at a 1:3 ratio. Cell-free culture supernatants were collected at different time points (i.e. 2, 4 and 6 days) and analyzed for p24 contents. Data shown represent the means±SD of triplicate samples from two different donors and are representative of three separate donors. Asterisks denote statistically significant data (*, $P<0.05$).

The connection between DCIR and the cis-infection pathway was confirmed using this experimental strategy (FIG. 4B).

In FIG. 4C, IM-MDDC were treated with Oligofectamine and then either left untreated (control) or exposed to a non-specific siRNA and a DCIR-specific siRNA. Cells ($2\times10^5$) were pulsed with NL4-3balenv (20 ng of p24) for 2 hrs at 37° C. After three washes with PBS to eliminate unbound virus, IM-MDDC were maintained in complete culture medium supplemented with GM-CSF and IL-4. Cell-free culture supernatants were collected at the indicated time points and analyzed for the p24 content. Data shown correspond to the means±SD of triplicate samples from two different donors and are representative of four separate donors. Asterisks denote statistically significant data (*, $P<0.05$; **, $P<0.01$).

The use of the DCIR-specific siRNA was found to decrease de novo virus production in IM-MDDC (FIG. 4C), which represents additional evidence that HIV-1 can use DCIR to achieve productive infection of this cell type.

Example 4

HIV-1 Replication in IM-MDDC is Reduced by Anti-DCIR Antibodies

In order to evaluate the potential role of DCIR in HIV infection, we used a second strategy, based on exposure of IM-MDDC to a polyclonal Ab specific for the COOH-terminal end of DCIR. Again, for the virus transfer assay, IM-MDDC were intentionally exposed to low doses of virions to better reflect the events occurring during mucosal transmission in vivo. Moreover, all virus stocks used in transmission assays were produced upon acute infection of primary human cells (i.e. PBMCs) to more closely parallel the natural microenvironment.

HIV-1 transmission by IM-MDDC was evaluated in the presence of a polyclonal Ab targeting the single carbohydrate recognition domain (CRD) in the extracellular COOH-terminal end of DCIR. The specificity of this Ab was monitored by flow cytometry using 293T cells transiently transfected with mammalian expression vectors coding for DCIR and DC-SIGN (data not shown).

In FIG. 5 left panels, IM-MDDC ($2\times10^5$ cells) were initially treated with either a control Ab or a polyclonal anti-DCIR (10 μg per $1.5\times10^5$ cells). Next, cells were extensively washed to eliminate excess Ab and pulsed with NL4-3balenv (20 ng of p24) for 2 hrs at 37° C. After three washes with PBS to eliminate unbound virus, IM-MDDC were maintained in complete culture medium supplemented with GM-CSF and IL-4. Cell-free culture supernatants were collected at the indicated time points and analyzed for the p24 content. Results obtained at 3 days post-infection are displayed in the small inserts. Data shown represent the means±SD of triplicate samples from two different donors and are representative of three separate donors. Asterisks denote statistically significant data (*, $P<0.05$; , $P<0.01$; *, $P<0.001$). In FIG. 5 right panels, IM-MDDC ($1\times10^5$ cells) were first treated with either a control Ab or a polyclonal anti-DCIR (10 μg per $1.5\times10^5$ cells). Cells were next washed to eliminate excess Ab and pulsed with NL4-3balenv (10 ng of p24) for 2 hrs at 37° C. After three washes with PBS to eliminate unbound virus, IM-MDDC were co-cultured with autologous CD4+ T cells at a 1:3 ratio. Cell-free culture supernatants were collected at day 2 following initiation of the co-culture and analyzed for the p24 content. Data shown represent the means±SD of triplicate samples from two distinct donors. Asterisks denote statistically significant data (**, $P<0.01$).

A decrease in virus replication was observed when IM-MDDC were acutely infected with HIV-1 in the presence of polyclonal anti-DCIR (FIG. 5, left panels). In addition, pretreatment of IM-MDDC with anti-DCIR before pulsing with HIV-1 and co-culture with autologous CD4+ T cells induced a significant decrease in HIV-1 transfer, as compared to transmission in the presence of a control Ab (FIG. 5, right panels). These results corroborate those obtained with DCIR-specific siRNAs and indicate that DCIR can act as a receptor for HIV-1 on the surface of IM-MDDC. Together, these results demonstrate that DCIR is involved in both trans- and cis-infection pathways mediated by DC.

Another experiment was carried out with an antibody which binds to amino acids 187 to 202 of DCIR (i.e., SSTF-WHPREPSDPNER; [SEQ ID NO:42]). Results of this experiment, demonstrate that this antibody is also capable of blocking HIV infection (FIG 5).

Example 5

DCIR-mediated Virus Capture and Infection-involvement of the Neck Domain of DCIR Previous studies have used the EBV genome-carrying B cell line Raji as a model system to reveal the role of DC-SIGN in HIV-1 capture and transmission[11]. To delineate the contribution of DCIR in HIV-1 capture and transfer, our next experiments were carried out using Raji-CD4, a Raji derivative that stably expresses CD4 and is highly susceptible to infection with X4-tropic strains of HIV-1[3].

Figure 6:
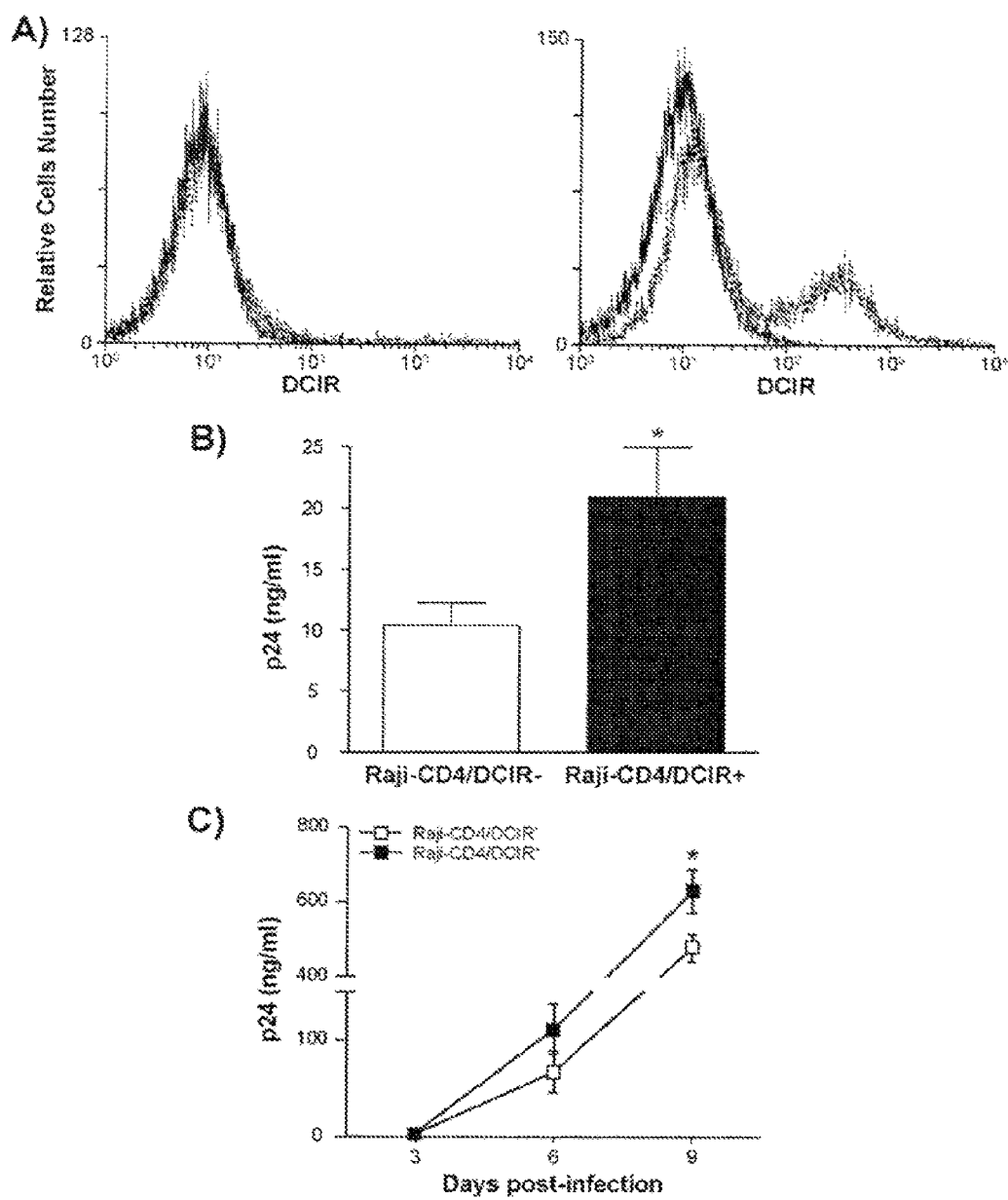
FIG. 6A illustrates DCIR expression as determined by flow cytometry analysis in Raji-CD4 cells nucleofected with an empty vector (left panel) or a DCIR-expressing vector (right panel)
FIG. 6B is an histogram illustrating virus associated with DCIR-negative Raji-CD4 cells or DCIR-positive Raji-CD4 cells.
FIG. 6C is an histogram illustrating virus production in HIV infected DCIR-negative Raji-CD4 cells or DCIR-positive Raji-CD4 cells.

In FIG. 6A, Raji-CD4 cells were nucleofected with either an empty control vector (left panel) or a mammalian expression vector coding for human DCIR (right panel). Five hours later, flow cytometry analysis of DCIR was performed using a combination of PE-labelled anti-DCIR Ab (dotted lines) and a control Ab (continuous lines). Data shown correspond to a single experiment representative of seven independent experiments. Transient expression of DCIR was thus achieved in Raji-CD4 using nucleofection (FIG. 6A), an electroporation-based method that is thought to target plasmid DNA directly to the cell nucleus.

In FIG. 6B, parental (DCIR-negative) and DCIR-expressing Raji-CD4 ($3 \times 10^6$ cells) were exposed to NL4-3 (300 ng of p24) for 60 min at 37° C. After three washes with PBS to remove unabsorbed virus, cell-associated virus was quantified by measuring the p24 content. Data shown correspond to the means±SD of triplicate samples from seven combined independent experiments. The asterisk denotes statistically significant data (*, $P<0.05$). As illustrated in FIG. 6B, binding of HIV-1 was increased in the presence of cell surface DCIR in Raji-CD4.

In FIG. 6C, parental (DCIR-negative) and DCIR-expressing Raji-CD4 ($1.5 \times 10^5$ cells) were exposed to NL4-3 (1.5 ng of p24) for 2 hrs at 37° C. After three washes with PBS to remove excess virus, cells were maintained in culture. Cell-free culture supernatants were collected at the indicated time points and assayed for the p24 content. Data shown correspond to the means±SD of triplicate samples from three combined independent experiments. The asterisk denotes statistically significant data (*, $P<0.05$). In addition, virus production was enhanced in DCIR-expressing Raji-CD4 as compared to the DCIR-negative parental cell line (FIG. 6C).

DCIR carries a neck region that is constituted of a variable number of 23-amino-acid tandem repeats. Previous observations suggest that DC-SIGN, which is closely related to DCIR, forms tetramers stabilized by the neck domain[12,13]. The importance of the neck portion in the observed phenomenon was addressed using a neck-deleted DCIR mutant (i.e. DCIRΔneck, where amino acids 66 to 100 are deleted).

Figure 7:
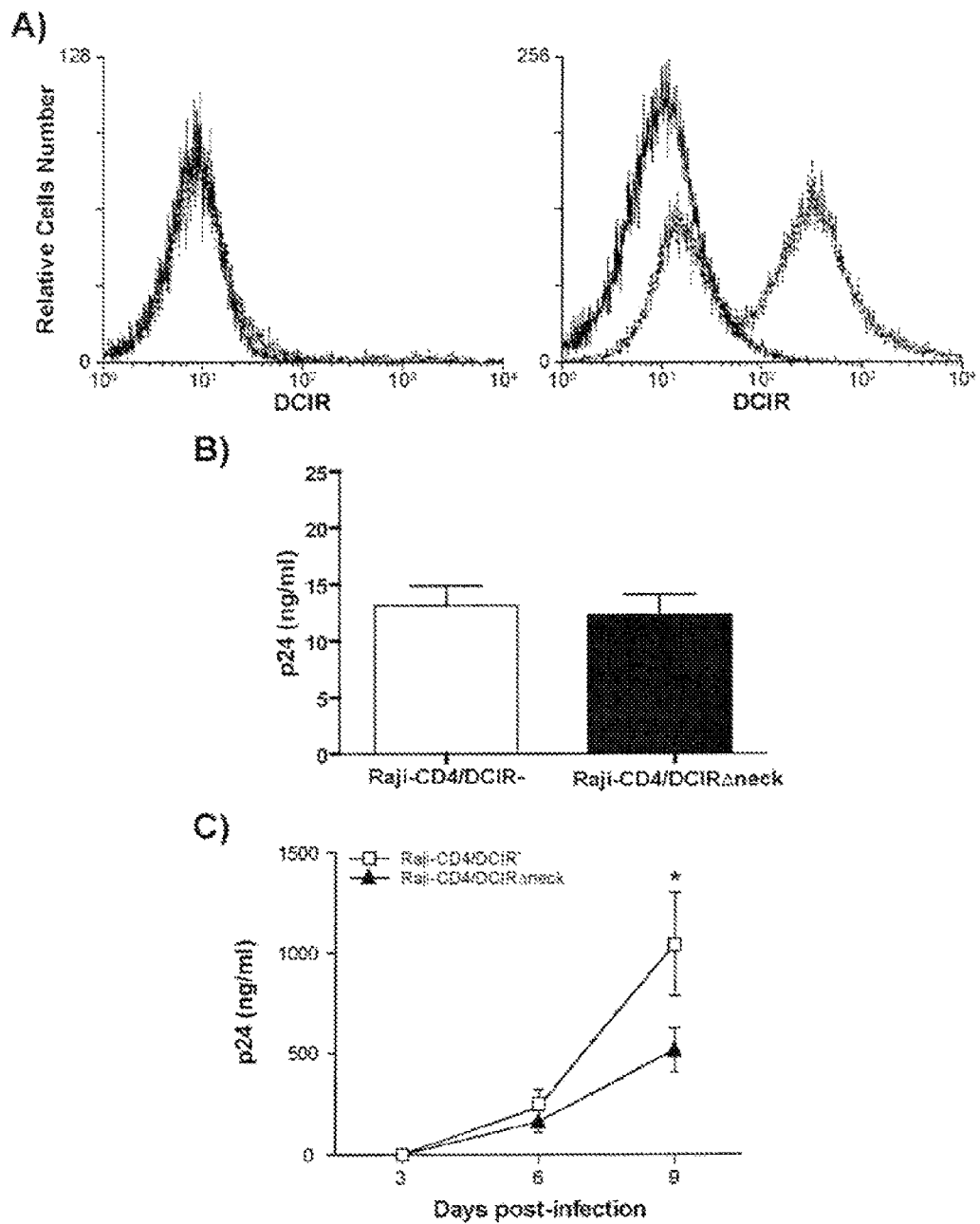
FIG. 7A illustrates cell surface expression of a mutated form of DCIR (DCIRΔneck) as determined by flow cytometry analysis in Raji-CD4 cells; left panel=cell nucleofected with an empty vector or right panel=cell nucleofected with DCIRΔneck-expressing vector.
FIG. 7B is an histogram illustrating cell-associated virus in DCIR-negative Raji-CD4 cells or DCIRΔneck-positive Raji-CD4 cells
FIG. 7C is an histogram illustrating virus production in HIV infected DCIR-negative Raji-CD4 cells or DCIRΔneck-positive Raji-CD4 cells.

In FIG. 7A Raji-CD4 cells were nucleofected with either an empty control vector (left panel) or a mammalian expression vector coding for a neck-deleted DCIR mutant (i.e. DCIRΔneck) (right panel). Five hours later, flow cytometry analysis of DCIR was performed using a combination of PE-labeled anti-DCIR monoclonal Ab (dotted lines) and a control Ab (continuous lines). Data shown correspond to a single experiment representative of five combined independent experiments. Nucleofection of Raji-CD4 with an expression vector coding for DCIRΔneck resulted in an efficient surface expression of the mutated DCIR (FIG. 7A).

In FIG. 7B, parental (DCIR-negative) and DCIRΔneck-expressing Raji-CD4 ($3 \times 10^6$ cells) were exposed to NL4-3 (300 ng of p24) for 60 min at 37° C. After three washes with PBS to remove unabsorbed virus, cell-associated virus was quantified by measuring the p24 content. Data shown correspond to the means±SD of triplicate samples from five combined independent experiments. Attachment of HIV-1 particles was not modulated following expression of DCIRΔneck on the surface of Raji-CD4 cells (FIG. 7B).

In FIG. 7C, parental (DCIR-negative) and DCIRΔneck-expressing Raji-CD4 ($1.5 \times 10^5$ cells) were exposed to NL4-3 (1.5 ng of p24) for 2 hrs at 37° C. After three washes with PBS to remove excess virus, cells were maintained in culture. Cell-free culture supernatants were collected at the indicated time points and assayed for the p24 content. Data shown correspond to the means±SD of triplicate samples and are representative of five combined independent experiments. The asterisk denotes statistically significant data (*, $P<0.05$).

In contrast to what was seen in cells expressing wild-type DICR (FIG. 6C), virus replication was not increased in the presence of DCIRΔneck on the cell surface of Raji-CD4 (FIG. 7C). However, expression of the neck-deleted DCIR mutant led to a reduction in virus replication, which might be due to reduced cell viability (data not shown). Data from these studies indicate that the neck region of DCIR plays a crucial role in its interaction with HIV-1.

Example 6

DCIR is Also Express on Apoptotic CD4+ T Cells

Figure 8:
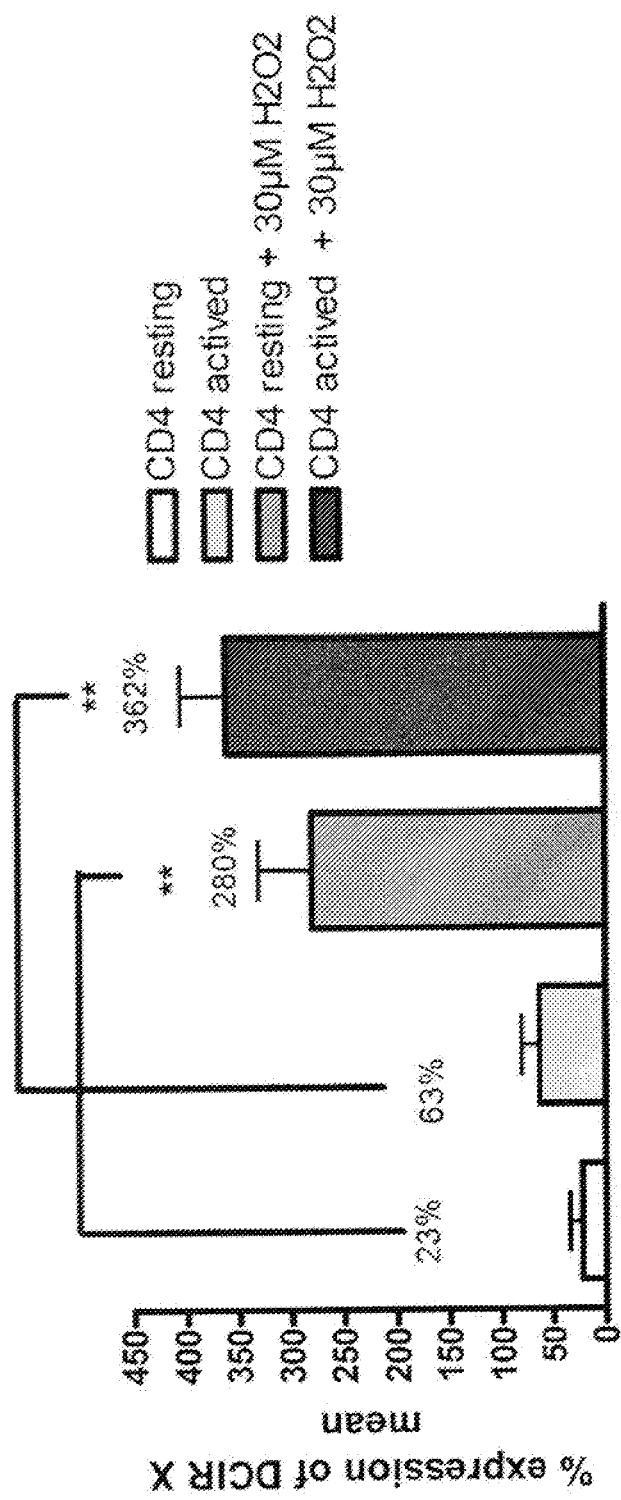
FIG. 8 is an histogram illustrating DCIR expression as determined by flow cytometry in resting or activated CD4+ T-cells and either left untreated or treated with hydrogen peroxide to induce apoptosis.

Purified CD4+ T cells from healthy patients were incubated with $H_2O_2$ (30 μM for 16 hrs) at $1 \times 10^6$ cells/ml in RPMI. DCIR expression was determined by flow cytometry analysis after staining with a commercial PE-conjugated anti-DCIR monoclonal Ab. FIG. 8, shows that DCIR is expressed on apoptotic CD4+ T cells.

We provide evidence that DCIR, a recently described CLR that is considered to be a DC-expressed activating immunoreceptor, can serve as an HIV-1 attachment factor on the surface of DC. The functional role played by DCIR in HIV-1 trans-infection of CD4+ T lymphocytes by DC was established through the use of specific siRNAs and a polyclonal Ab. Additional studies indicated that DCIR-mediated virus transfer to CD4+ T cells also involves de novo replication of HIV-1 in DC (i.e. the second phase of the transfer process). We provide evidence that the DCIR-mediated effect on virus propagation is not linked with a diminished capacity of DC to cause proliferation of CD4+ T cells. Moreover, our studies suggest that DCIR-mediated HIV-1 attachment and subsequent transmission requires the neck domain of DCIR.

Although the present invention has been described herein by way of exemplary embodiments, it can be modified without departing from the scope and the nature of the invention.

The present description refers to a number of documents, the content of which is herein incorporated by reference in their entirety.

References

1. Richard M, Thibault N, Veilleux P, Breton R, Beaulieu A D. The ITIM-bearing CLECSF6 (DCIR) is down-modulated in neutrophils by neutrophil activating agents. Biochem Biophys Res Commun. 2003; 310:767-773.
2. Gilbert C, Barat C, Cantin R, Tremblay M J. Involvement of Src and Syk tyrosine kinases in HIV-1 transfer from dendritic cells to CD4+ T lymphocytes. J. Immunol. 2007; 178:2862-2871.
3. Cantin R, Fortin J F, Lamontagne G, Tremblay M. The presence of host-derived HLA-DR1 on human immunodeficiency virus type 1 increases viral infectivity. J. Virol. 1997; 71:1922-1930.
4. Dornadula G, Zhang H, Shetty S, Pomerantz R J. HIV-1 virions produced from replicating peripheral blood lymphocytes are more infectious than those from nonproliferating macrophages due to higher levels of intravirion reverse transcripts: implications for pathogenesis and transmission. Virology. 1999; 253:10-16.
5. Bounou S, Dumais N, Tremblay M J. Attachment of human immunodeficiency virus-1 (HIV-1) particles bearing host-encoded B7-2 proteins leads to nuclear factor-kappa B- and nuclear factor of activated T cells-dependent activation of HIV-1 long terminal repeat transcription. J Biol. Chem. 2001; 276:6359-6369.
6. Zar J H. *Biostatistical Analysis:* 2nd edn. Englewood Cliffs: Prentice-Hall International, Inc., 1984.
7. Bates E E, Fournier N, Garcia E, et al. APCs express DCIR, a novel C-type lectin surface receptor containing an immunoreceptor tyrosine-based inhibitory motif J. Immunol. 1999; 163:1973-1983.
8. Turville S G, Cameron P U, Handley A, et al. Diversity of receptors binding HIV on dendritic cell subsets. Nat. Immunol. 2002; 3:975-983.
9. Turville S G, Santos J J, Frank I, et al. Immunodeficiency virus uptake, turnover, and 2-phase transfer in human dendritic cells. Blood. 2004; 103:2170-2179.
10. Moris A, Pajot A, Blanchet F, Guivel-Benhassine F, Salcedo M, Schwartz O. Dendritic cells and HIV-specific CD4+ T cells: HIV antigen presentation, T-cell activation, and viral transfer. Blood. 2006; 108:1643-1651.
11. Wu L, Martin T D, Carrington M, KewalRamani V N. Raji B cells, misidentified as THP-1 cells, stimulate DC-SIGN-mediated HIV transmission. Virology. 2004; 318:17-23.
12. Feinberg H, Guo Y, Mitchell D A, Drickamer K, Weis W I. Extended neck regions stabilize tetramers of the receptors DC-SIGN and DC-SIGNR. J Biol Chem. 2005; 280: 1327-1335.
13. Mitchell D A, Fadden A J, Drickamer K. A Novel Mechanism of Carbohydrate Recognition by the C-type Lectins DC-SIGN and DC-SIGNR. Subunit Organization and Binding to Multivalent Ligands. J Biol Chem. 2001; 276: 28939-28945.

The invention claimed is:

1. A method for inhibiting dendritic cell immunoreceptor (DCIR) mediated human immunodeficiency virus (HIV) infection in a DCIR-expressing cell, the method comprising administering to a mammal in need thereof an anti-DCIR antibody or an antigen binding fragment thereof, wherein said anti-DCIR antibody or antigen binding fragment binds specifically to a region of human DCIR defined by amino acids 187-202 of SEQ ID NO:6 or amino acids 223-237 of SEQ ID NO:6.

2. The method of claim 1, wherein said antibody or antigen binding fragment binds specifically to a carboxy terminal region of human DCIR.

3. The method of claim 1, wherein said antibody or antigen binding fragment binds specifically to a human DCIR epitope comprising at least 5 amino acids of human DCIR.

4. The method of claim 1, wherein said antibody or antigen binding fragment binds specifically to a human DCIR epitope comprising from 5 to 15 amino acids of SEQ ID NO.:10 or from 5 to 16 amino acids of SEQ ID NO.:42.

5. The method of claim 1, wherein said antibody or antigen binding fragment is capable of competing with an antibody specific of an epitope comprising from 5 to 15 amino acids of SEQ ID NO.:10 or with an antibody specific of an epitope comprising from 5 to 16 amino acids of SEQ ID NO.:42.

6. The method of claim 1, wherein said antibody is a polyclonal antibody or a monoclonal antibody.

7. The method of claim 1, wherein the DCIR-expressing cell is a dendritic cell or a CD4+T-lymphocyte.

8. The method of claim 1, wherein said HIV is human immunodeficiency virus type-1 (HIV-1).

9. The method of claim 1, wherein said antibody or antigen binding fragments is administered prior to contacting the DCIR-expressing cell with HIV.

10. The method of claim 1, wherein said antibody or antigen binding fragment interferes with transfer of HIV from dendritic cells to CD4+cells.

11. The method of claim 1, wherein said anti-DCIR antibody or antigen binding fragment thereof specifically inhibits cell surface interaction between HIV and DCIR.

12. A method for inhibiting dendritic cell immunoreceptor (DCIR)-mediated human immunodeficiency virus (HIV) infection in a DCIR-expressing cell, the method comprising contacting said DCIR-expressing cell with an anti-DCIR antibody or an antigen binding fragment thereof, wherein said anti-DCIR antibody or antigen binding fragment binds specifically to a region of human DCIR defined by amino acids 187-202 of SEQ ID NO:6 or amino acids 223-237 of SEQ ID NO:6.

13. The method of claim 12, wherein the DCIR-expressing cell is a dendritic cell or a CD4+T-lymphocyte.

14. The method of claim 12, wherein, the DCIR-expressing cell is a human DCIR-expressing cell.

15. The method of claim 12, wherein said HIV is human immunodeficiency virus type-1 (HIV-1).

16. The method of claim 12, wherein said antibody or antigen binding fragment is administered prior to contacting the DCIR-expressing cell with HIV.

17. A method for inhibiting dendritic cell immunoreceptor (DCIR)-mediated attachment or binding of a human immunodeficiency virus (HIV) to a DCIR-expressing cell, the method comprising contacting said DCIR-expressing cell with an anti-DCIR antibody or an antigen binding fragment thereof, wherein said anti-DCIR antibody or antigen binding fragment binds specifically to a region of human DCIR defined by amino acids 187-202 of SEQ ID NO:6 or amino acids 223-237 of SEQ ID NO:6.

18. The method of claim 17, wherein the DCIR-expressing cell is a dendritic cell or a CD4+T-lymphocyte.

19. The method of claim 17, wherein the DOR-expressing cell is a human DCIR-expressing cell.

20. The method of claim 17, wherein said HIV is human immunodeficiency virus type-1 (HIV-1).

21. The method of claim 17, wherein the DCIR-expressing cell is contacted with said antibody or antigen binding fragment prior to exposure to HIV.

\* \* \* \* \*

```
                        SEQUENCE LISTING

<160> NUMBER OF SEQ ID NOS: 45

<210> SEQ ID NO 1
<211> LENGTH: 1290
<212> TYPE: DNA
<213> ORGANISM: Homo sapiens
<300> PUBLICATION INFORMATION:
<301> AUTHORS: Elisabeth E. M. Bates et al.
<302> TITLE: APCs Express DCIR, a novel C-Type Lectin Surface Receptor
       Containing an Immunoreceptor Tyrosine-Based Inhibitory Motif
<303> JOURNAL: J. Immunol.
<304> VOLUME: 163
<305> ISSUE: 4
<306> PAGES: 1973-1983
<307> DATE: 1999-08-15

<400> SEQUENCE: 1
tgtgattctc actatactgg tcctgaggaa agggcttctg tgaactgcgg tttttagttt      60
ttattgtggt tcttagttct catgagaccc ctcttgagga tatgtgccta tctggtgcct     120
ctgctctcca ctagttgagt gaaaggaagg aggtaattta ccaccatgtt tggttcctgt     180
ttataagatg ttttaagaaa gatttgaaac agatttctct aagaaagcag aagctctctt     240
cccattatga cttcggaaat cacttatgct gaagtgaggt tcaaaaatga attcaagtcc     300
tcaggcatca acacagcctc ttctgcagct tccaaggaga ggactgcccc tcacaaaagt     360
aataccggat tccccaagct gctttgtgcc tcactgttga tattttcct gctattggca      420 atctcattct ttattgcttt tgtcattttc tttcaaaaat attctcagct tcttgaaaaa     480
aagactacaa aagagctggt tcatacaaca ttggagtgtg tgaaaaaaaa tatgcccgtg     540
gaagagacag cctggagctg ttgcccaaag aattggaagt catttagttc caactgctac     600
tttatttcta ctgaatcagc atcttggcaa gacagtgaga aggactgtgc tagaatggag     660
gctcacctgc tggtgataaa cactcaagaa gagcaggatt tcatcttcca gaatctgcaa     720
```

```
gaagaatctg cttattttgt ggggctctca gatccagaag gtcagcgaca ttggcaatgg    780
gttgatcaga caccatacaa tgaaagttcc acattctggc atccacgtga gcccagtgat    840
cccaatgagc gctgcgttgt gctaaatttt cgtaaatcac ccaaaagatg gggctggaat    900
gatgttaatt gtcttggtcc tcaaaggtca gtttgtgaga tgatgaagat ccacttatga    960
actgaacatt ctccatgaac aggtggttgg attggtatct gtcattgtag ggatagataa   1020
taagctcttc ttattcatgt gtaagggagg tccatagaat ttaggtggtc tgtcaactat   1080
tctacttatg agagaattgg tctgtacatt gactgattca cttttcata aagtgagcat   1140 ttattgagca ttttttcatg tgccagagcc tgtactggag gcccccattg tgcacacatg   1200
gagagaacat gagtctctct taattttat ctggttgcta aagaattatt taccaataaa   1260
attatatgat gtggtgtctc aaaaaaaaaa                                    1290
```

<210> SEQ ID NO 2
<211> LENGTH: 714
<212> TYPE: DNA
<213> ORGANISM: Homo sapiens
<300> PUBLICATION INFORMATION:
<301> AUTHORS: Elisabeth E.M. Bates et al.,
<302> TITLE: APCs Express DCIR, a novel C-Type Lectin Surface Receptor
       Containing an Immunoreceptor Tyrosine-Based Inhibitory Motif
<303> JOURNAL: J. Immunol.
<304> VOLUME: 163
<305> ISSUE: 4
<306> PAGES: 1973-1984
<307> DATE: 1999-08-15

<400> SEQUENCE: 2

```
atgacttcgg aaatcactta tgctgaagtg aggttcaaaa atgaattcaa gtcctcaggc     60
atcaacacag cctcttctgc agcttccaag gagaggactg cccctcacaa aagtaatacc    120
ggattcccca agctgctttg tgcctcactg ttgatatttt tcctgctatt ggcaatctca    180
ttctttattg cttttgtcat tttctttcaa aaatattctc agcttcttga aaaaaagact    240
acaaaagagc tggttcatac aacattggag tgtgtgaaaa aaatatgcc cgtggaagag    300 acagcctgga gctgttgccc aaagaattgg aagtcattta gttccaactg ctactttatt    360
tctactgaat cagcatcttg gcaagacagt gagaaggact gtgctagaat ggaggctcac    420
ctgctggtga taaacactca agaagagcag gatttcatct tccagaatct gcaagaagaa    480
tctgcttatt ttgtggggct ctcagatcca aaggtcagc gacattggca atgggttgat    540
cagacaccat acaatgaaag ttccacattc tggcatccac gtgagcccag tgatcccaat    600
gagcgctgcg ttgtgctaaa ttttcgtaaa tcacccaaaa gatggggctg aatgatgtt    660 aattgtcttg gtcctcaaag gtcagtttgt gagatgatga agatccactt atga          714
```

<210> SEQ ID NO 3
<211> LENGTH: 615
<212> TYPE: DNA
<213> ORGANISM: Homo sapiens
<300> PUBLICATION INFORMATION:
<301> AUTHORS: Ronninger M. et al.,
<302> TITLE: Differential Expression of Transcripts for the
       Autoimmunity-related Dencritic Cell Immonureceptor
<303> JOURNAL: Genes Immun.
<304> VOLUME: 9
<305> ISSUE: 5
<306> PAGES: 412-418
<307> DATE: 2008-05-15
<308> DATABASE ACCESSION NUMBER: NM_016184
<309> DATABASE ENTRY DATE: 2008-05-15
<313> RELEVANT RESIDUES IN SEQ ID NO: (1)..(615)

<400> SEQUENCE: 3

```
atgacttcgg aaatcactta tgctgaagtg aggttcaaaa atgaattcaa gtcctcaggc      60
atcaacacag cctcttctgc agcttccaag gagaggactg cccctcacaa aagtaatacc     120
ggattcccca agctgctttg tgcctcactg ttgatatttt tcctgctatt ggcaatctca     180
ttctttattg cttttgtcaa gacagcctgg agctgttgcc caaagaattg gaagtcattt     240
agttccaact gctactttat ttctactgaa tcagcatctt ggcaagacag tgagaaggac     300
tgtgctagaa tggaggctca cctgctggtg ataaacactc aagaagagca ggatttcatc     360
ttccagaatc tgcaagaaga atctgcttat tttgtggggc tctcagatcc agaaggtcag     420
cgacattggc aatgggttga tcagacacca tacaatgaaa gttccacatt ctggcatcca     480
cgtgagccca gtgatcccaa tgagcgctgc gttgtgctaa attttcgtaa atcacccaaa     540
agatggggct ggaatgatgt taattgtctt ggtcctcaaa ggtcagtttg tgagatgatg     600
aagatccact tatga                                                      615
```

<210> SEQ ID NO 4
<211> LENGTH: 597
<212> TYPE: DNA
<213> ORGANISM: Homo sapiens
<300> PUBLICATION INFORMATION:
<301> AUTHORS: Ronninger M. et al.,
<302> TITLE: Differential Expression of Transcripts for the
    Autoimmunity-related Dendritic Cell Immunoreceptor
<303> JOURNAL: Genes Immun.
<304> VOLUME: 9
<305> ISSUE: 5
<306> PAGES: 412-418
<307> DATE: 2008-05-15
<308> DATABASE ACCESSION NUMBER: NM_194450
<309> DATABASE ENTRY DATE: 2008-05-15
<313> RELEVANT RESIDUES IN SEQ ID NO: (1)..(597)

<400> SEQUENCE: 4

```
atgacttcgg aaatcactta tgctgaagtg aggttcaaaa atgaattcaa gtcctcaggc      60
atcaacacag cctcttctgc agttttcttt caaaaatatt ctcagcttct tgaaaaaaag     120
actacaaaag agctggttca tacaacattg gagtgtgtga aaaaaaatat gcccgtggaa     180
gagacagcct ggagctgttg cccaaagaat tggaagtcat ttagttccaa ctgctacttt     240
atttctactg aatcagcatc ttggcaagac agtgagaagg actgtgctag aatggaggct     300
cacctgctgg tgataaacac tcaagaagag caggatttca tcttccagaa tctgcaagaa     360
gaatctgctt attttgtggg gctctcagat ccagaaggtc agcgacattg gcaatgggtt     420
gatcagacac catacaatga agttccacat tctggcatc cacgtgagcc cagtgatccc     480
aatgagcgct gcgttgtgct aaattttcgt aaatcaccca aaagatgggg ctggaatgat     540
gttaattgtc ttggtcctca aaggtcagtt tgtgagatga tgaagatcca cttatga       597
```

<210> SEQ ID NO 5
<211> LENGTH: 498
<212> TYPE: DNA
<213> ORGANISM: Homo sapiens
<300> PUBLICATION INFORMATION:
<301> AUTHORS: Ronninger M. et al.,
<302> TITLE: Differential Expression of Transcripts for the
    Autoimmunity-related Dendritic Cell Immunoreceptor
<303> JOURNAL: Genes Immun.
<304> VOLUME: 9
<305> ISSUE: 5
<306> PAGES: 412-418
<307> DATE: 2008-05-15
<308> DATABASE ACCESSION NUMBER: NM_194448
<309> DATABASE ENTRY DATE: 2008-05-15

<313> RELEVANT RESIDUES IN SEQ ID NO: (1)..(498)

<400> SEQUENCE: 5

```
atgacttcgg aaatcactta tgctgaagtg aggttcaaaa atgaattcaa gtcctcaggc      60
atcaacacag cctcttctgc agagacagcc tggagctgtt gcccaaagaa ttggaagtca     120
tttagttcca actgctactt tatttctact gaatcagcat cttggcaaga cagtgagaag     180
gactgtgcta aatggaggc tcacctgctg gtgataaaca ctcaagaaga gcaggatttc     240
```
atcttccaga atctgcaaga gaatctgct tattttgtgg ggctctcaga tccagaaggt     300
cagcgacatt ggcaatgggt tgatcagaca ccatacaatg aaagttccac attctggcat     360
ccacgtgagc ccagtgatcc aatgagcgc tgcgttgtgc taaattttcg taaatcaccc     420
aaaagatggg gctggaatga tgttaattgt cttggtcctc aaaggtcagt ttgtgagatg     480
atgaagatcc acttatga                                                    498

<210> SEQ ID NO 6
<211> LENGTH: 237
<212> TYPE: PRT
<213> ORGANISM: Homo sapiens
<300> PUBLICATION INFORMATION:
<301> AUTHORS: Elisabeth E. M. BATES
<302> TITLE: APCs Express DCIR, a novel C-Type Lectin Surface Receptor
      Containing an Immunoreceptor Tyrosine-Based Inhibitory Motif
<303> JOURNAL: J. Immunol.
<304> VOLUME: 163
<305> ISSUE: 4
<306> PAGES: 1973-1983
<307> DATE: 1999-08-15

<400> SEQUENCE: 6

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro His Lys Ser Asn Thr Gly Phe Pro Lys Leu Leu Cys Ala
        35                  40                  45

Ser Leu Leu Ile Phe Phe Leu Leu Ala Ile Ser Phe Phe Ile Ala
    50                  55                  60

Phe Val Ile Phe Phe Gln Lys Tyr Ser Gln Leu Leu Glu Lys Lys Thr
65                  70                  75                  80

Thr Lys Glu Leu Val His Thr Thr Leu Glu Cys Val Lys Lys Asn Met
                85                  90                  95

Pro Val Glu Glu Thr Ala Trp Ser Cys Cys Pro Lys Asn Trp Lys Ser
            100                 105                 110

Phe Ser Ser Asn Cys Tyr Phe Ile Ser Thr Glu Ser Ala Ser Trp Gln
        115                 120                 125

Asp Ser Glu Lys Asp Cys Ala Arg Met Glu Ala His Leu Leu Val Ile
    130                 135                 140

Asn Thr Gln Glu Glu Gln Asp Phe Ile Phe Gln Asn Leu Gln Glu Glu
145                 150                 155                 160

Ser Ala Tyr Phe Val Gly Leu Ser Asp Pro Glu Gly Gln Arg His Trp
                165                 170                 175

Gln Trp Val Asp Gln Thr Pro Tyr Asn Glu Ser Ser Thr Phe Trp His
            180                 185                 190

Pro Arg Glu Pro Ser Asp Pro Asn Glu Arg Cys Val Val Leu Asn Phe
        195                 200                 205

Arg Lys Ser Pro Lys Arg Trp Gly Trp Asn Asp Val Asn Cys Leu Gly
    210                 215                 220

```
Pro Gln Arg Ser Val Cys Glu Met Met Lys Ile His Leu
225                 230                 235

<210> SEQ ID NO 7
<211> LENGTH: 204
<212> TYPE: PRT
<213> ORGANISM: Homo sapiens
<300> PUBLICATION INFORMATION:
<301> AUTHORS: Ronninger, M. et al.,
<302> TITLE: Differential Expression of Transcripts for the
      Autoimmunity-related Human Dendritic Cell Immunoreceptor
<303> JOURNAL: Genes Immun.
<304> VOLUME: 9
<305> ISSUE: 5
<306> PAGES: 412-418
<307> DATE: 2008-05-15
<308> DATABASE ACCESSION NUMBER: NM_194450
<309> DATABASE ENTRY DATE: 2008-05-15
<313> RELEVANT RESIDUES IN SEQ ID NO: (1)..(204)

<400> SEQUENCE: 7

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro His Lys Ser Asn Thr Gly Phe Pro Lys Leu Leu Cys Ala
        35                  40                  45

Ser Leu Leu Ile Phe Phe Leu Leu Ala Ile Ser Phe Phe Ile Ala
    50                  55                  60

Phe Val Lys Thr Ala Trp Ser Cys Cys Pro Lys Asn Trp Lys Ser Phe
65              70                  75                  80

Ser Ser Asn Cys Tyr Phe Ile Ser Thr Glu Ser Ala Ser Trp Gln Asp
                85                  90                  95

Ser Glu Lys Asp Cys Ala Arg Met Glu Ala His Leu Leu Val Ile Asn
            100                 105                 110

Thr Gln Glu Glu Gln Asp Phe Ile Phe Gln Asn Leu Gln Glu Glu Ser
        115                 120                 125

Ala Tyr Phe Val Gly Leu Ser Asp Pro Glu Gly Gln Arg His Trp Gln
    130                 135                 140

Trp Val Asp Gln Thr Pro Tyr Asn Glu Ser Ser Thr Phe Trp His Pro
145                 150                 155                 160

Arg Glu Pro Ser Asp Pro Asn Glu Arg Cys Val Val Leu Asn Phe Arg
                165                 170                 175

Lys Ser Pro Lys Arg Trp Gly Trp Asn Asp Val Asn Cys Leu Gly Pro
            180                 185                 190

Gln Arg Ser Val Cys Glu Met Met Lys Ile His Leu
        195                 200

<210> SEQ ID NO 8
<211> LENGTH: 198
<212> TYPE: PRT
<213> ORGANISM: Homo sapiens
<300> PUBLICATION INFORMATION:
<301> AUTHORS: Ronninger, M. et al.,
<302> TITLE: Differential Expressiono f Transcripts for the
      Autoimmunity-related Human Dendritic Cell Immunoreceptor
<303> JOURNAL: Genes Immun.
<304> VOLUME: 9
<305> ISSUE: 5
<306> PAGES: 412-418
<307> DATE: 2008-05-15
<308> DATABASE ACCESSION NUMBER: NM_19447
<309> DATABASE ENTRY DATE: 2008-05-15
<313> RELEVANT RESIDUES IN SEQ ID NO: (1)..(198)
```

<400> SEQUENCE: 8

```
Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Val Phe Phe Gln Lys
            20                  25                  30

Tyr Ser Gln Leu Leu Glu Lys Lys Thr Thr Lys Glu Leu Val His Thr
        35                  40                  45

Thr Leu Glu Cys Val Lys Lys Asn Met Pro Val Glu Glu Thr Ala Trp
    50                  55                  60

Ser Cys Cys Pro Lys Asn Trp Lys Ser Phe Ser Ser Asn Cys Tyr Phe
65                  70                  75                  80

Ile Ser Thr Glu Ser Ala Ser Trp Gln Asp Ser Glu Lys Asp Cys Ala
                85                  90                  95

Arg Met Glu Ala His Leu Leu Val Ile Asn Thr Gln Glu Glu Gln Asp
            100                 105                 110

Phe Ile Phe Gln Asn Leu Gln Glu Glu Ser Ala Tyr Phe Val Gly Leu
        115                 120                 125

Ser Asp Pro Glu Gly Gln Arg His Trp Gln Trp Val Asp Gln Thr Pro
    130                 135                 140

Tyr Asn Glu Ser Ser Thr Phe Trp His Pro Arg Glu Pro Ser Asp Pro
145                 150                 155                 160

Asn Glu Arg Cys Val Val Leu Asn Phe Arg Lys Ser Pro Lys Arg Trp
                165                 170                 175

Gly Trp Asn Asp Val Asn Cys Leu Gly Pro Gln Arg Ser Val Cys Glu
            180                 185                 190

Met Met Lys Ile His Leu
        195
```

<210> SEQ ID NO 9
<211> LENGTH: 165
<212> TYPE: PRT
<213> ORGANISM: Homo sapiens
<300> PUBLICATION INFORMATION:
<301> AUTHORS: Ronninger, M. et al.,
<302> TITLE: Differential Expression of Transcripts for the
    Autoimmunity-related Dendritic Cell Immunoreceptor
<303> JOURNAL: Genes Immun.
<304> VOLUME: 9
<305> ISSUE: 5
<306> PAGES: 412-418
<307> DATE: 2008-05-15
<308> DATABASE ACCESSION NUMBER: NM_194448
<309> DATABASE ENTRY DATE: 2008-05-15
<313> RELEVANT RESIDUES IN SEQ ID NO: (1)..(165)

<400> SEQUENCE: 9

```
Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Glu Thr Ala Trp Ser
            20                  25                  30

Cys Cys Pro Lys Asn Trp Lys Ser Phe Ser Ser Asn Cys Tyr Phe Ile
        35                  40                  45

Ser Thr Glu Ser Ala Ser Trp Gln Asp Ser Glu Lys Asp Cys Ala Arg
    50                  55                  60

Met Glu Ala His Leu Leu Val Ile Asn Thr Gln Glu Glu Gln Asp Phe
65                  70                  75                  80

Ile Phe Gln Asn Leu Gln Glu Glu Ser Ala Tyr Phe Val Gly Leu Ser
                85                  90                  95
```

```
Asp Pro Glu Gly Gln Arg His Trp Gln Trp Val Asp Gln Thr Pro Tyr
            100                 105                 110
Asn Glu Ser Ser Thr Phe Trp His Pro Arg Glu Pro Ser Asp Pro Asn
        115                 120                 125
Glu Arg Cys Val Val Leu Asn Phe Arg Lys Ser Pro Lys Arg Trp Gly
    130                 135                 140
Trp Asn Asp Val Asn Cys Leu Gly Pro Gln Arg Ser Val Cys Glu Met
145                 150                 155                 160
Met Lys Ile His Leu
                165

<210> SEQ ID NO 10
<211> LENGTH: 15
<212> TYPE: PRT
<213> ORGANISM: Artificial sequence
<220> FEATURE:
<223> OTHER INFORMATION: Synthetic: DCIR epitope

<400> SEQUENCE: 10

Leu Gly Pro Gln Arg Ser Val Cys Glu Met Met Lys Ile His Leu
1               5                   10                  15

<210> SEQ ID NO 11
<211> LENGTH: 17
<212> TYPE: DNA
<213> ORGANISM: Artificial sequence
<220> FEATURE:
<223> OTHER INFORMATION: Synthesized

<400> SEQUENCE: 11
atttaggtgg tctgtca                                                  17

<210> SEQ ID NO 12
<211> LENGTH: 21
<212> TYPE: DNA
<213> ORGANISM: Artificial sequence
<220> FEATURE:
<223> OTHER INFORMATION: Synthesized

<400> SEQUENCE: 12
aagggaggtc catagaattt a                                             21

<210> SEQ ID NO 13
<211> LENGTH: 21
<212> TYPE: DNA
<213> ORGANISM: Artificial sequence
<220> FEATURE:
<223> OTHER INFORMATION: Synthesized

<400> SEQUENCE: 13
tcggaaatca cttatgctga a                                             21

<210> SEQ ID NO 14
<211> LENGTH: 21
<212> TYPE: DNA
<213> ORGANISM: Artificial sequence
<220> FEATURE:
<223> OTHER INFORMATION: Synthesized

<400> SEQUENCE: 14
ctggtgataa acactcaaga a                                             21

<210> SEQ ID NO 15
<211> LENGTH: 21
<212> TYPE: DNA
```

<213> ORGANISM: Artificial sequence
<220> FEATURE:
<223> OTHER INFORMATION: Synthesized

<400> SEQUENCE: 15
gacagcctgg agctgttgcc c                                    21

<210> SEQ ID NO 16
<211> LENGTH: 21
<212> TYPE: DNA
<213> ORGANISM: Artificial sequence
<220> FEATURE:
<223> OTHER INFORMATION: Synthesized

<400> SEQUENCE: 16
tactgaatca gcatcttggc a                                    21

<210> SEQ ID NO 17
<211> LENGTH: 21
<212> TYPE: DNA
<213> ORGANISM: Artificial sequence
<220> FEATURE:
<223> OTHER INFORMATION: Synthesized

<400> SEQUENCE: 17
gacagtgaga aggactgtgc t                                    21

<210> SEQ ID NO 18
<211> LENGTH: 21
<212> TYPE: DNA
<213> ORGANISM: Artificial sequence
<220> FEATURE:
<223> OTHER INFORMATION: Synthesized

<400> SEQUENCE: 18
cagatccaga aggtcagcga c                                    21

<210> SEQ ID NO 19
<211> LENGTH: 21
<212> TYPE: DNA
<213> ORGANISM: Artificial sequence
<220> FEATURE:
<223> OTHER INFORMATION: Synthesized

<400> SEQUENCE: 19
cagaaggtca gcgacattgg c                                    21

<210> SEQ ID NO 20
<211> LENGTH: 21
<212> TYPE: DNA
<213> ORGANISM: Artificial sequence
<220> FEATURE:
<223> OTHER INFORMATION: Synthesized

<400> SEQUENCE: 20
aaagggcttc tgtgaactgc g                                    21

<210> SEQ ID NO 21
<211> LENGTH: 21
<212> TYPE: DNA
<213> ORGANISM: Artificial sequence
<220> FEATURE:
<223> OTHER INFORMATION: Synthesized

<400> SEQUENCE: 21
aagggcttct gtgaactgcg g                                    21

```
<210> SEQ ID NO 22
<211> LENGTH: 21
<212> TYPE: DNA
<213> ORGANISM: Artificial sequence
<220> FEATURE:
<223> OTHER INFORMATION: Synthesized

<400> SEQUENCE: 22
aagcagaagc tctcttccca t                                              21

<210> SEQ ID NO 23
<211> LENGTH: 21
<212> TYPE: DNA
<213> ORGANISM: Artificial sequence
<220> FEATURE:
<223> OTHER INFORMATION: Synthesized

<400> SEQUENCE: 23
aagctctctt cccattatga c                                              21

<210> SEQ ID NO 24
<211> LENGTH: 21
<212> TYPE: DNA
<213> ORGANISM: Artificial sequence
<220> FEATURE:
<223> OTHER INFORMATION: Synthesized

<400> SEQUENCE: 24
aacacagcct cttctgcagc t                                              21

<210> SEQ ID NO 25
<211> LENGTH: 21
<212> TYPE: DNA
<213> ORGANISM: Artificial sequence
<220> FEATURE:
<223> OTHER INFORMATION: Synthesized

<400> SEQUENCE: 25
aaggagagga ctgcccctca c                                              21

<210> SEQ ID NO 26
<211> LENGTH: 21
<212> TYPE: DNA
<213> ORGANISM: Artificial sequence
<220> FEATURE:
<223> OTHER INFORMATION: Synthesized

<400> SEQUENCE: 26
aagagacagc ctggagctgt t                                              21

<210> SEQ ID NO 27
<211> LENGTH: 21
<212> TYPE: DNA
<213> ORGANISM: Artificial sequence
<220> FEATURE:
<223> OTHER INFORMATION: Synthesized

<400> SEQUENCE: 27
aagtcattta gttccaactg c                                              21

<210> SEQ ID NO 28
<211> LENGTH: 21
<212> TYPE: DNA
<213> ORGANISM: Artificial sequence
<220> FEATURE:
<223> OTHER INFORMATION: Synthesized
```

```
<400> SEQUENCE: 28
aagacagtga gaaggactgt g                                              21

<210> SEQ ID NO 29
<211> LENGTH: 21
<212> TYPE: DNA
<213> ORGANISM: Artificial sequence
<220> FEATURE:
<223> OTHER INFORMATION: Synthesized

<400> SEQUENCE: 29
aagaagagca ggatttcatc t                                              21

<210> SEQ ID NO 30
<211> LENGTH: 21
<212> TYPE: DNA
<213> ORGANISM: Artificial sequence
<220> FEATURE:
<223> OTHER INFORMATION: Synthesized

<400> SEQUENCE: 30
aagagcagga tttcatcttc c                                              21

<210> SEQ ID NO 31
<211> LENGTH: 21
<212> TYPE: DNA
<213> ORGANISM: Artificial sequence
<220> FEATURE:
<223> OTHER INFORMATION: Synthesized

<400> SEQUENCE: 31
aagaatctgc ttattttgtg g                                              21

<210> SEQ ID NO 32
<211> LENGTH: 21
<212> TYPE: DNA
<213> ORGANISM: Artificial sequence
<220> FEATURE:
<223> OTHER INFORMATION: Synthesized

<400> SEQUENCE: 32
aagttccaca ttctggcatc c                                              21

<210> SEQ ID NO 33
<211> LENGTH: 21
<212> TYPE: DNA
<213> ORGANISM: Artificial sequence
<220> FEATURE:
<223> OTHER INFORMATION: Synthesized

<400> SEQUENCE: 33
aagatggggc tggaatgatg t                                              21

<210> SEQ ID NO 34
<211> LENGTH: 21
<212> TYPE: DNA
<213> ORGANISM: Artificial sequence
<220> FEATURE:
<223> OTHER INFORMATION: Synthesized

<400> SEQUENCE: 34
aaaggtcagt ttgtgagatg a                                              21

<210> SEQ ID NO 35
<211> LENGTH: 21
<212> TYPE: DNA
```

```
<213> ORGANISM: Artificial sequence
<220> FEATURE:
<223> OTHER INFORMATION: Synthesized

<400> SEQUENCE: 35
aaggtcagtt tgtgagatga t                                              21

<210> SEQ ID NO 36
<211> LENGTH: 21
<212> TYPE: DNA
<213> ORGANISM: Artificial sequence
<220> FEATURE:
<223> OTHER INFORMATION: Synthesized

<400> SEQUENCE: 36
aagatccact tatgaactga a                                              21

<210> SEQ ID NO 37
<211> LENGTH: 21
<212> TYPE: DNA
<213> ORGANISM: Artificial sequence
<220> FEATURE:
<223> OTHER INFORMATION: Synthesized

<400> SEQUENCE: 37
aactgaacat tctccatgaa c                                              21

<210> SEQ ID NO 38
<211> LENGTH: 21
<212> TYPE: DNA
<213> ORGANISM: Artificial sequence
<220> FEATURE:
<223> OTHER INFORMATION: Synthesized

<400> SEQUENCE: 38
aacaggtggt tggattggta t                                              21

<210> SEQ ID NO 39
<211> LENGTH: 21
<212> TYPE: DNA
<213> ORGANISM: Artificial sequence
<220> FEATURE:
<223> OTHER INFORMATION: Synthesized

<400> SEQUENCE: 39
aagctcttct tattcatgtg t                                              21

<210> SEQ ID NO 40
<211> LENGTH: 21
<212> TYPE: DNA
<213> ORGANISM: Artificial sequence
<220> FEATURE:
<223> OTHER INFORMATION: Synthesized

<400> SEQUENCE: 40
aaagtgagca tttattgagc a                                              21

<210> SEQ ID NO 41
<211> LENGTH: 21
<212> TYPE: DNA
<213> ORGANISM: Artificial sequence
<220> FEATURE:
<223> OTHER INFORMATION: Synthesized

<400> SEQUENCE: 41
aagtgagcat ttattgagca t                                              21
```

```
<210> SEQ ID NO 42
<211> LENGTH: 16
<212> TYPE: PRT
<213> ORGANISM: Artificial sequence
<220> FEATURE:
<223> OTHER INFORMATION: Synthetic : EPS epitope

<400> SEQUENCE: 42

Ser Ser Thr Phe Trp His Pro Arg Glu Pro Ser Asp Pro Asn Glu Arg
1               5                   10                  15

<210> SEQ ID NO 43
<211> LENGTH: 17
<212> TYPE: PRT
<213> ORGANISM: Artificial sequence
<220> FEATURE:
<223> OTHER INFORMATION: Synthetic: epitope

<400> SEQUENCE: 43

Arg Lys Ser Pro Lys Arg Trp Gly Trp Asn Asp Val Asn Cys Leu Gly
1               5                   10                  15

Pro

<210> SEQ ID NO 44
<211> LENGTH: 33
<212> TYPE: PRT
<213> ORGANISM: Artificial sequence
<220> FEATURE:
<223> OTHER INFORMATION: Synthetic: epitope

<400> SEQUENCE: 44

Ile Phe Phe Gln Lys Tyr Ser Gln Leu Leu Glu Lys Lys Thr Thr Lys
1               5                   10                  15

Glu Leu Val His Thr Thr Leu Glu Cys Val Lys Lys Asn Met Pro Val
            20                  25                  30

Glu

<210> SEQ ID NO 45
<211> LENGTH: 21
<212> TYPE: DNA
<213> ORGANISM: Artificial sequence
<220> FEATURE:
<223> OTHER INFORMATION: Synthesized

<400> SEQUENCE: 45
aattctccga aggtgtcacg t                                           21
```